United States Patent [19]

Lasher et al.

[11] Patent Number: 5,720,154

[45] Date of Patent: Feb. 24, 1998

[54] ENHANCED DRUG DISPENSING SYSTEM

[75] Inventors: Christopher J. Lasher, Ridgewood; Dennis Wayne Rice, Union; Michael Joseph Szesko, Freehold, all of N.J.; Michael L. Mahar, Wurtsboro, N.Y.

[73] Assignee: Medco Containment Services, Inc., Montvale, N.J.

[21] Appl. No.: 455,402

[22] Filed: May 31, 1995

(Under 37 CFR 1.47)

Related U.S. Application Data

[63] Continuation of Ser. No. 250,435, May 27, 1994, abandoned.

[51] Int. Cl.⁶ .......................... B65B 57/00; B65B 57/18; B65B 57/20
[52] U.S. Cl. .......................... 53/411; 53/168; 53/495; 53/501; 53/508
[58] Field of Search .................. 53/168, 500, 501, 53/508, 507, 495, 493, 77, 237, 131.4, 131.2, 411, 475, 473

[56] References Cited

U.S. PATENT DOCUMENTS

| | | | |
|---|---|---|---|
| 2,618,420 | 11/1952 | Levine | 53/505 |
| 3,139,713 | 7/1964 | Merrill et al. | 53/55 |
| 3,193,196 | 7/1965 | Merrill et al. | 53/501 X |
| 3,677,437 | 7/1972 | Haigler | 221/7 |
| 4,013,192 | 3/1977 | Pillon | 221/7 |
| 4,018,358 | 4/1977 | Johnson et al. | 221/7 |
| 4,112,332 | 9/1978 | Veith et al. | 315/169 |
| 4,171,065 | 10/1979 | Hurst | 221/7 |
| 4,664,289 | 5/1987 | Shimizu et al. | 221/2 |
| 4,674,259 | 6/1987 | Hills | 53/202 |
| 4,695,954 | 9/1987 | Rose et al. | 364/413 |
| 4,733,362 | 3/1988 | Hataguchi | 364/479 |
| 4,847,764 | 7/1989 | Halvorson | 364/413.02 |
| 4,869,394 | 9/1989 | Hurst | 221/7 |
| 4,870,799 | 10/1989 | Bergerioux et al. | 53/168 X |
| 4,953,745 | 9/1990 | Rowlett, Jr. | 221/5 |
| 5,097,652 | 3/1992 | Inamura | 53/168 X |
| 5,208,762 | 5/1993 | Charhut et al. | 364/478 |
| 5,348,061 | 9/1994 | Riley et al. | 221/2 X |
| 5,481,855 | 1/1996 | Yuyama | 53/493 |
| 5,502,944 | 4/1996 | Kraft et al. | 53/168 X |

OTHER PUBLICATIONS

"Baker Lockouts: Persistence Pays Off", *Quality Bulletin*, Mar. 1993.

*Primary Examiner*—James F. Coan
*Attorney, Agent, or Firm*—Lane, Aitken & McCann

[57] ABSTRACT

In an automated prescription pill dispensing system, a multiplicity of pill dispensers are provided each operable to count out and dispense pills from supply hoppers. The dispensers are controlled by a computer which selects up to five of the dispensers to operate and control the selected pill dispensers to count out pills simultaneously. The pill dispensers dispense the pills into the first set of output hoppers, from which the pills can be released into a second output hopper under the control of the computer. The computer will release the pills from the second output hopper corresponding to a selected pill dispenser through a snout into a pill vial in response to sensing the presence of a pill vial at the snout. The computer controls a prescription label printer to print prescription labels for the pill vials. The computer also controls indicator lights to indicate which dispensing cell is selected and ready to have pills released from the second output hopper corresponding thereto. Automatically controlled security doors control access to supply hoppers for each of the pill dispensers.

27 Claims, 17 Drawing Sheets

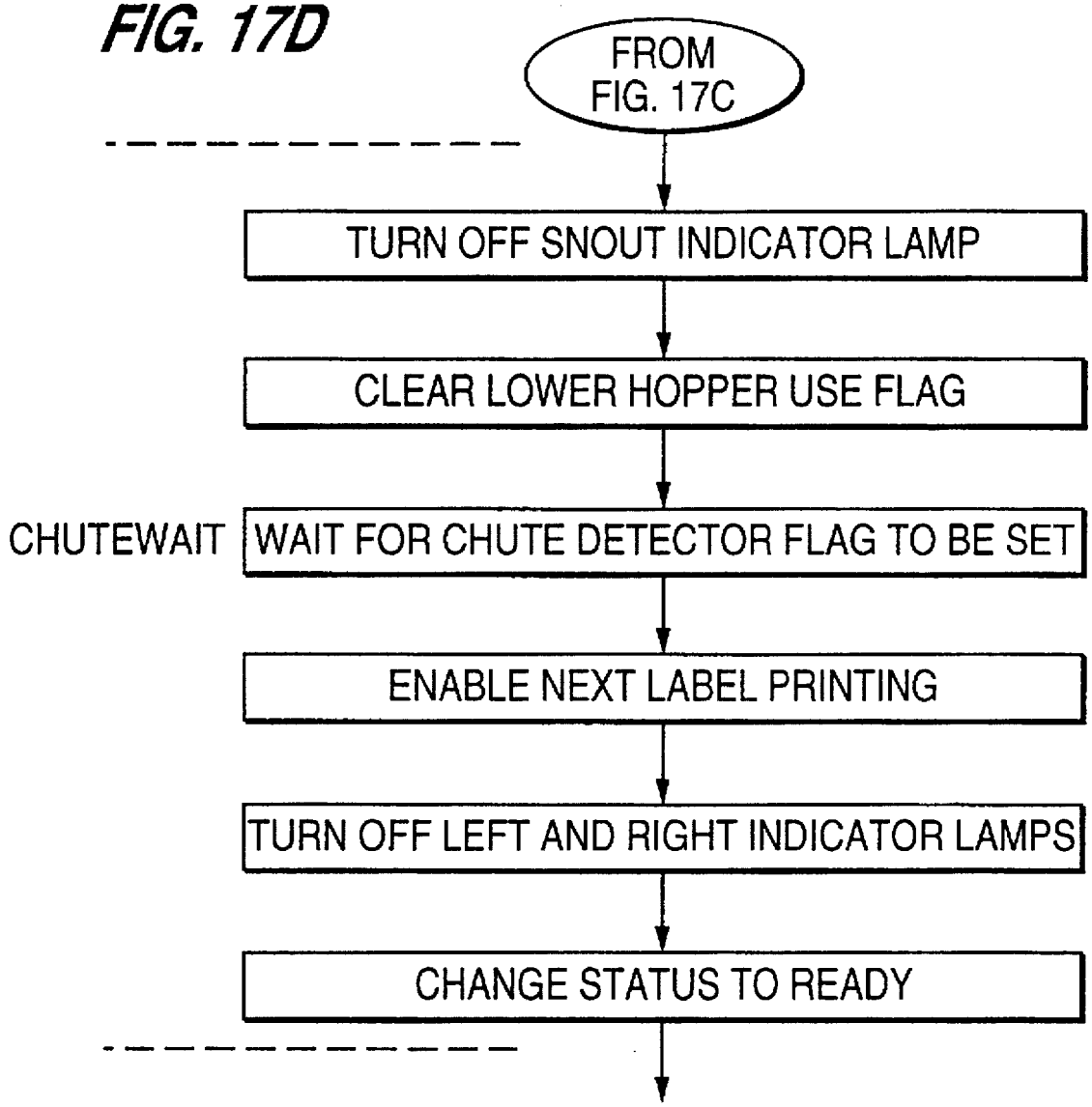

ENHANCED DRUG DISPENSING SYSTEM

This application is a continuation application of application Ser. No. 08/250,435, filed May 27, 1994, now abandoned.

BACKGROUND OF THE INVENTION

The present invention relates to a system for dispensing articles and, more particularly, to a system for dispensing different drugs in the form of pills, capsules, etc. with high speed and with the assurance that the right amount of drug is dispensed into the proper container associated with a particular drug prescription.

Devices are known for precisely counting and dispensing drugs, such as the device disclosed in U.S. Pat. No. 4,111,332. It is known to use a plurality of such counting and dispensing devices, each associated with one drug, to fill large numbers of prescriptions. However, the need for filling large numbers of prescriptions at high speed has exceeded the capacity of mere banks of such devices. It has been found that the article counting and dispensing devices require too frequent filling with the drugs to be dispensed and that the time for dispensing the drugs to fill a prescription is too slow.

Idle time in the operation of such devices as presently employed is caused by the fact that the operator must now wait on the average of 12 seconds for every prescription filled. Another 25% of time is spent replenishing the counting and dispensing devices with drugs. The operator must obtain the bottles of drugs, break the seals, open each bottle, and remove desiccants and packing material. The operator opens a cabinet in which a counting and dispensing device is contained, moves the device to a position in which the device projects from the cabinet, and removes a fill cap on the device. The contents of the drug bottles are emptied into the hopper of the counting and dispensing device, filling the hopper to the recommended capacity. The operator then replaces the fill cap, moves the device back into the cabinet in its dispensing position, and disposes of drug bottles, caps, cotton, desiccants and other dunnage. This procedure is followed for each of the counting and dispensing devices, wherein one drug is associated with each of the devices.

SUMMARY OF THE INVENTION

In order to overcome the drawbacks of the known counting and dispensing devices, the present invention provides additional structure and controls to be used with such devices. The enhancements to the known counting and dispensing devices include a backfill replenishment system, a front buffer assembly, a new arrangement for the operator station, and a novel control system.

In preparation for the operation of the system according to the present invention, prescriptions go through an order entry sequence which includes data entry, protocol management, professional review, and order scheduling. The system according to the present invention then fills the orders in cooperation with an operator.

The backfill replenishment system provides a much larger volume of pill storage for the known counting and dispensing devices. It provides access and security for replenishing the drugs in the counting and dispensing devices from the backside of a cabinet in which the devices are positioned. It provides replenishment of the drugs to the counting and the dispensing devices without the need for opening the front of the cabinet and moving the counting and dispensing devices to a projecting position. The backfill replenishment is accomplished by a panel provided for the counting and dispensing devices at the rear of the cabinet and a hopper for feeding each of the counting and dispensing devices. The hoppers replenish the drugs to the counting and dispensing devices on an as-needed basis. A sensor in the hopper indicates to the control system when replenishment is required.

Also provided for each of the counting and dispensing devices is a front buffer assembly which receives the drugs from the associated counting and dispensing device. The front buffer assembly includes a first, upper chamber, which receives the pills or the like from the counting and dispensing device. The control system transfers the pills from the upper chamber to a second, lower chamber. The pills are then available to the operator by contacting the associated dispensing snout with an appropriate receptacle.

The system according to the present invention includes an operator station including a console equipped with a key pad, display monitor, label printer, and hands-free bar code reader, as well as pill bottles, bottle caps and cotton provided in bins having indicator lamps known as pick-to-lights. Additional indicator lamps are provided, respectively, on the left and right sides of the work station to indicate whether the next order for delivery will be available to the left or the right of the operator console. The system further includes an indicator lamp at each of a plurality of dispensing snouts to indicate at which dispensing snout the order will be available for delivery. The order is delivered into a receptacle when the operator places the receptacle in contact with the appropriate dispensing snout.

In operation, using the bar-code scanner to scan a bar code on the operator's personal identification badge, the operator signs on to a computer embodying the control system. A prescription label containing a bar-coded label for the next prescription to be filled is printed by the label printer on a command from the control system. The indicator lamp associated with the bin holding the appropriate receptacle flashes. The operator places the label on the container and verifies to the control system the bar code on the label by using the hands-free bar code reader. The indicator lamp associated with either the left side or the right side of the operator workstation flashes to indicate the general area where the next order will be delivered. The indicator lamp associated with the particular dispensing snout where the order will be delivered also flashes. The operator fills the order by engaging the indicated snout with the receptacle. The system will not release the drugs into the receptacles without bar code verification by the bar code reader, thus assuring that the proper drugs go into the proper receptacle. The operator puts cotton into the container and a cap onto the container and places the container into a delivery chute. It is contemplated that the operating station can include a large plurality of counting and dispensing devices in increments of six devices arranged in a vertical slice through the cabinet and an unlimited number of slices each containing six dispensing units can be provided at one workstation, with each dispensing device having a dispensing snout at a convenient dispensing height.

Another person at the backside of the cabinet fills the hoppers supplying the counting and dispensing devices. The filling is done independently of the dispensing and without interfering with the dispensing operation. When a counting and dispensing device requires replenishment, the technician at the back of the cabinet reads with a scanner, which can be of the hand-held type, a bar-coded label on a bulk supply container of drugs. In response to the reading, the control system causes an indicator lamp to flash adjacent to a security door of the hopper for the counting and dispensing device used to fill orders for the drug whose container label was scanned. All of the security doors are initially locked. The scanning of the bulk container label also releases the lock of the appropriate security door so that access to the supply hopper protected by the door is permitted. After the supply hopper is filled, the security door is closed, whereupon it locks automatically. Unless the security door is closed, all of the other security doors remain locked, and access to any other supply hopper is denied. In case of a malfunction of any of the counting and dispensing units, the malfunctioning unit is removed through the back wall of the cabinet and replaced with a spare unit. The removed unit can be repaired without interrupting the dispensing operation. Removal can only be done by an authorized technician as each dispensing unit is locked into place by the control system.

Upon a command from the dispensing control system, the counting and dispensing device counts a desired number of pills and advances them to a buffer assembly. The buffer assembly includes an upper hopper having a solenoid-operated outlet door, which releases the pills in the upper hopper into a lower hopper, also having a solenoid-operated outlet door. The pills are released from the lower hopper in response to the presence of the receptacle at the dispensing snout, the pills falling from the lower hopper through a tube to the dispensing snout.

Dispensing of drug orders is accomplished in less than half the time as in previously known systems. Also with the present invention, there is no operator waiting time for pills to be counted.

BRIEF DESCRIPTION OF THE DRAWINGS

FIGS. 17A through 17D show a diagram illustrating the sequence of operations performed by the computer in filling a given prescription.

DETAILED DESCRIPTION OF THE PREFERRED EMBODIMENT

Figure 1:
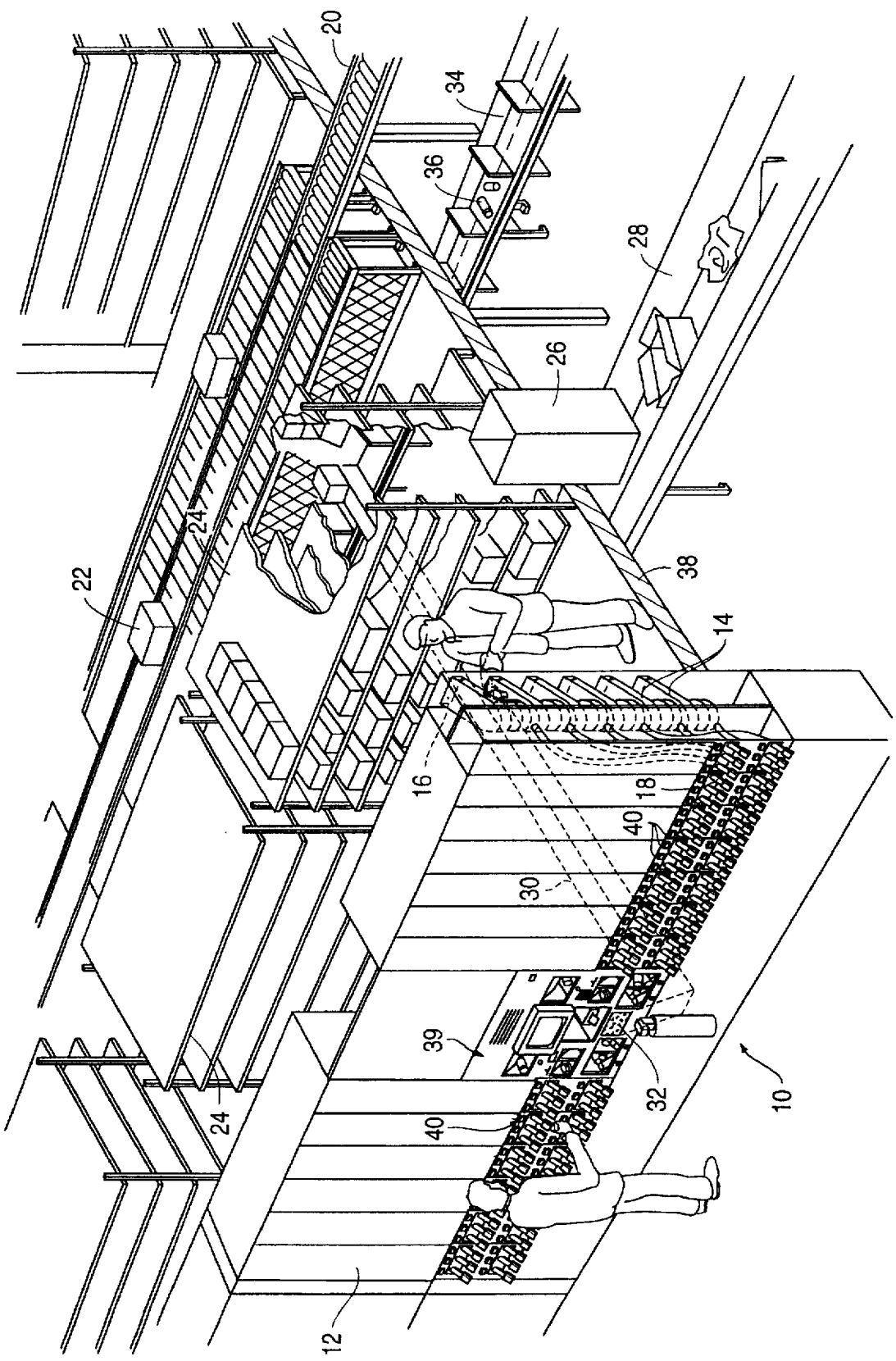
FIG. 1 is a perspective view of a prescription filling operation including the drug dispensing system according to the present invention.

As can be seen from FIG. 1, the enhanced drug dispensing system according to the present invention, which is designated generally by the reference numeral 10, can be employed as a part of a larger, high volume prescription filling and distribution operation. The dispensing system 10 includes one or more cabinets 12, each containing a large plurality of dispensing subsystems or subassemblies 14, each of which has an inlet 16 at the rear of the cabinet and a dispensing snout 18 at the front of the cabinet. The cabinet 12 comprises a plurality of modules 19, each defined by a vertical slice through the cabinet in which a plurality, for example six, of the dispensing subassemblies are arranged, one above another. An operator at a workstation at the front of the cabinet 12 controls the dispensing operation with the help of a control system embodied in a computer. The replenishment of the drugs at the rear of the cabinet 12 is performed by a technician, also in cooperation with the control system. It can be seen that a conveyor 20 is provided so that boxes 22 of drugs from the manufacturers can be received at the prescription filling and distribution center. Storage shelves 24 are provided at the rear of the cabinet 12 so that a large volume supply of all drugs are on hand. A waste disposal chute 26 can be provided which leads to a waste conveyor 28 for removing dunnage from the drug replenishment area. A chute 30 having an inlet 32 at the front side of the cabinet 12 leads to one or more conveyors 34 for transporting filled prescription receptacles 36 to a packing and shipping area. A sensor 37 (FIG. 2), such as a photocell, is positioned at the inlet 32 of the chute 30 to send a signal to the control system that a filled drug receptacle 36 has been deposited in the chute after the receptacle has been filled with the prescription drug. In the prescription filling and distribution center illustrated in FIG. 1, the drug replenishment technician stands on a platform 38 raised above the level of the surface on which the dispensing system operator stands. The near end of the platform 38 is shown broken away in FIGS. 1 and 2 to illustrate the height of the platform above the floor of the workstation and to show, in FIG. 1, the conveyors 28 and 34 below the platform. A wall at the near end of the cabinet 12 and a portion of the top of the cabinet are omitted in order to show the arrangement of dispensing subsystems 14 in the slice or module 19 at the near end of the cabinet.

Figure 2:
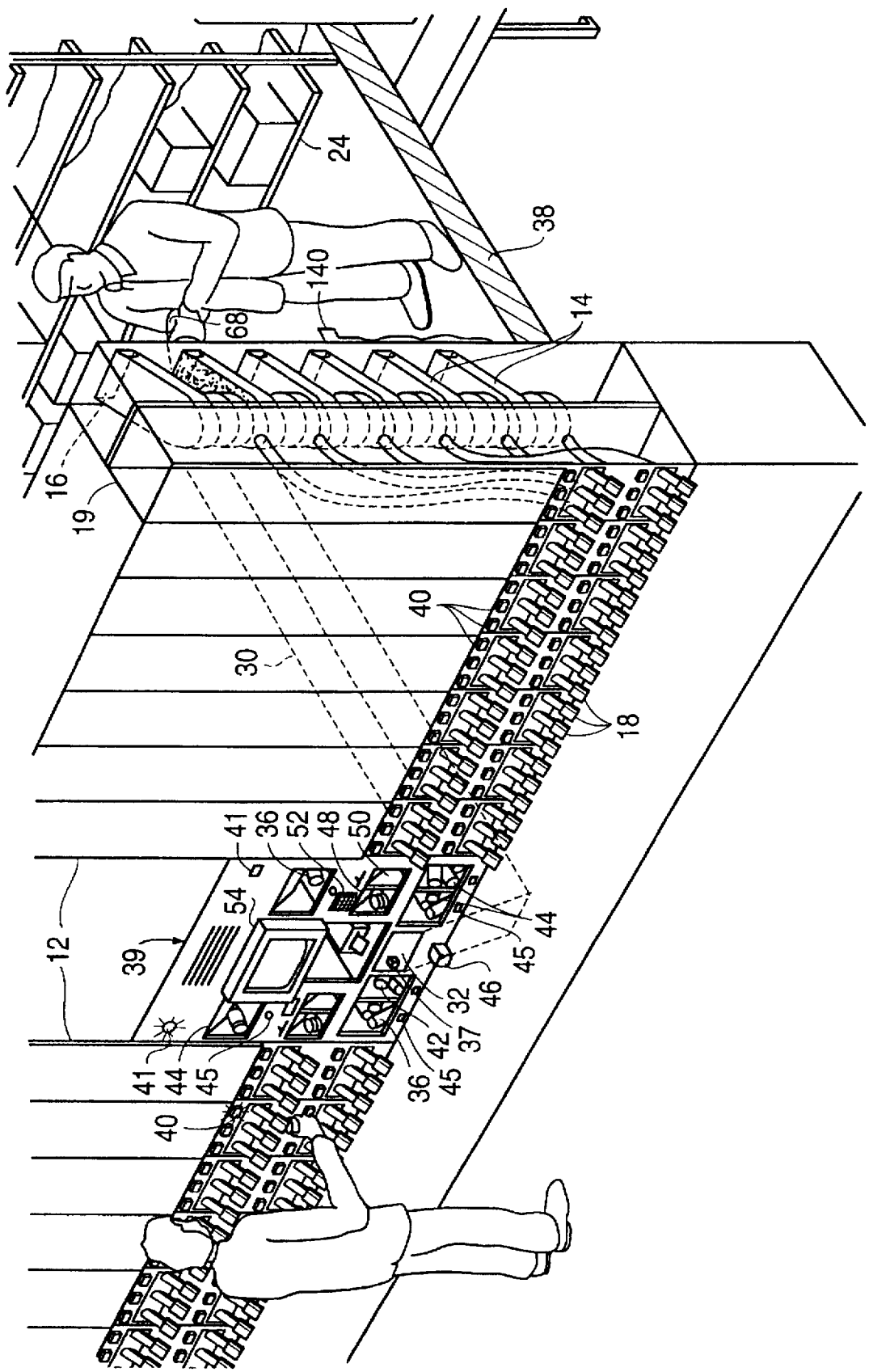
FIG. 2 is an enlarged perspective view of the drug dispensing system of FIG. 1, including an operator console.

As can best be seen from FIG. 2, the operator work station includes a console 39 provided at the front side of the cabinet 12 containing the dispensing subsystems 14. The dispensing snouts 18 of the dispensing subsystems 14 project through the forward wall of the cabinet 12 and are arranged in close proximity to one another in order to minimize the amount of movement required by the operator to reach all of the snouts. The dispensing snouts 18 are also positioned at heights convenient for the operator to fill a receptacle 36 from them. For each module 19, the dispensing snouts are arranged, for example, in two horizontal rows of three snouts each. An indicator lamp 40 is positioned adjacent to each dispensing snout 18 to indicate to the operator the snout through which the next pill delivery will take place. There is also an indicator lamp 41 on each side of the console 39 to indicate the area of the operator station where the next pill delivery will occur. Centrally located at the console 39 is a printer 42 which provides, one by one, labels associated with a series of prescriptions to be filled, each label bearing a bar code representing a unique prescription number identifying the prescription being filled. A plurality of bins 44 are provided adjacent to the printer 42 for containing a variety of sizes of pill receptacles 36, so that the appropriate size receptacle can be used for each of the prescriptions to be filled. Each bin 44 holds one specific size of receptacle 36, and an indicator lamp 45 is located at each bin to signal the operator which bin holds receptacles suitable for receiving the next prescription to be dispensed. The console 39 also has a hands-free bar code reader 46 for reading the bar codes on the labels supplied by the printer 42. The delivery chute 30 receives the labeled, filled receptacles 36, each holding pills filling a specific prescription. Compartments 48 and 50 holding container caps and cotton are also provided at the console 39. Bin labels (not shown) are provided at each of the bins 44, 48 and 50 to indicate whether receptacles 36, caps or cotton are in the bin and, in the case of the receptacles and the caps, to indicate the size of the receptacles or caps in the bin. A computer keypad 52 is located at the console 39 so that the operator may sign-on to the computer and thereby enable the dispensing control system. A computer monitor 54 is also positioned in the console 39. A transparent pill sample case 55 is provided adjacent to each of the dispensing snouts 18 to serve as a check that the pills being dispensed from the dispensing snout 18 are the pills which should be dispensed from that dispensing snout. A sample pill is placed in the transparent sample case 55 as a reference for comparison with the pills issuing from the dispensing snout 18. A discrepancy between the sample pill and the dispensed pills is an indication that one or the other is incorrect. A similar sample case containing a sample pill is provided at each inlet 16 at the rear of the cabinet as will be described below.

As can be seen from FIGS. 3–6, a large supply hopper 56 is mounted at the inlet 16 to the dispensing subsystem 14 in order to hold a large supply of pills so that the frequency of human-assisted filling of the dispensing subsystem is greatly reduced. The supply hopper 56 is supported on a conventional counting and dispensing device or cell 58 so that the supply hopper slopes from back to front. The counting and dispensing device 58 is mounted in the cabinet 12 at approximately the same slope from back to front as the supply hopper 56. The supply hopper 56 is generally a rectangular parallelepiped having a top 60, a bottom 62, a rear end 64, and a forward end 66, and sides 67, except that the supply hopper tapers at its forward end. The rear end 64 of the supply hopper 56 is open to receive pills from bulk containers 68 (FIG. 2) in which the pills are shipped from the factory. At the forward end 66 of the supply hopper 56, the sides 67 of the hopper are angled toward one another to guide the pills in the hopper to an outlet opening 69 in the bottom 62 of the hopper at the forward end 66. The top 60 of the supply hopper 56 has a portion which is angled upward, from front to rear, with respect to the bottom 62 of the hopper, and a rear wall 70 projects upwardly at an oblique angle relative to the bottom of the hopper, so that the opening at the rear end 64 of the hopper is angled upward for receiving the pills from their bulk containers 68.

The outlet opening 69 of the supply hopper 56 feeds the inlet of the conventional counting and dispensing cell 58, which inlet could, in conventional use, receive pills directly from their bulk containers 68. Suitable counting and dispensing cells are disclosed in U.S. Pat. Nos. 4,111,332 and 4,869,394 and are available under the trademark BAKER CELLS from Automated Prescription Systems, Inc. of Pineville, La. Such counting and dispensing cells each have their own, circular rotating hopper mounted on a support and rotated by connection with a drive shaft of a motor projecting through the support. The bottom of the rotating hopper is undercut to form a circumvential series of radial, angularly spaced pill receiving slots, with the innermost ends of the slots overlying an outlet opening in the support. Upon rotation of the hopper, the pills move along the slots, and each pill trips a switch before falling through the outlet opening in order to count each pill as it is dispensed. When the accumulated count of dispensed pills equals a preselected count, operation of the cell is stopped.

Figure 6:
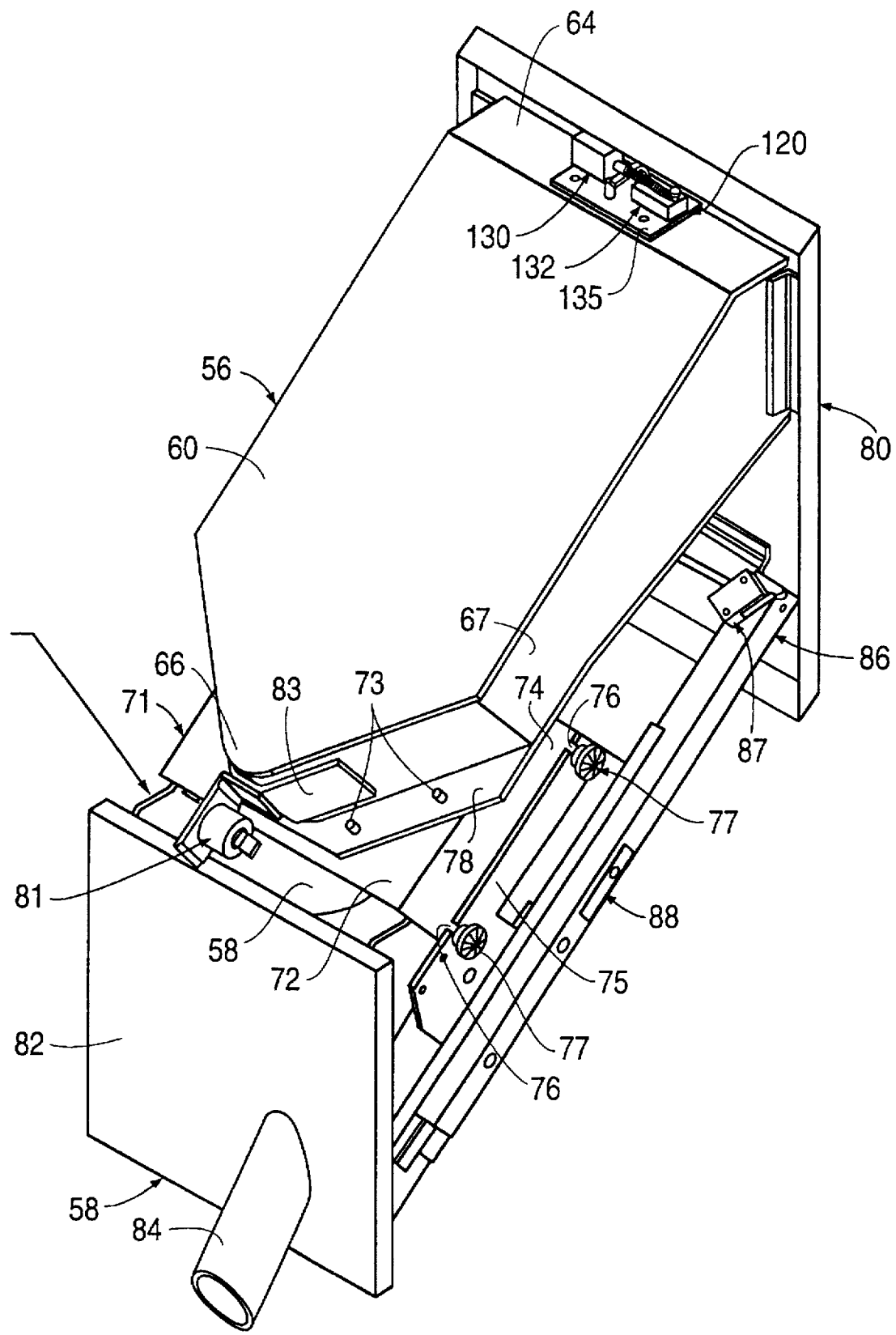
FIG. 6 is an enlarged perspective view of an assembly of the supply hopper and an associated counting and dispensing device of FIG. 3.

As can best be seen from FIG. 6, the supply hopper 56 is mounted above the counting and dispensing cell 58 by means of a bracket 71 having an inverted U-shape. The bracket 71 has a base portion 72 from which studs 73 project upwardly and sides 74 which extend down for connection to plates 75. The base portion defines an opening (not shown) which is positioned for alignment with the outlet opening 70 in the supply hopper 56, so that pills can pass from the supply hopper to the counting and dispensing cell 58. Each plate 75 defines upwardly open slots 76 for receiving thumb screws 77 projecting laterally from the sides of the bracket. A forwardly extending flange 78 at the forward end 66 of the supply hopper 56 defines apertures which receive the studs 73 on the bracket 71.

The rear end 64 of the supply hopper 56 is connected to a rear panel 80. The rear panel 80 is positioned within an opening in the rear wall of the cabinet 12 so that the rear panel fits flush with the rear wall. A vibrator 81 for the supply hopper 56 is mounted on a front panel 82 connected with the counting and dispensing cell 58 and is connected to an angle plate 83 in which the tapering forward end 66 of the supply hopper 56 nestles. Operation of the vibrator 81 assures that the pills in the supply hopper 56 move through the outlet opening 69 into the counting and dispensing cell 58.

Figure 3:
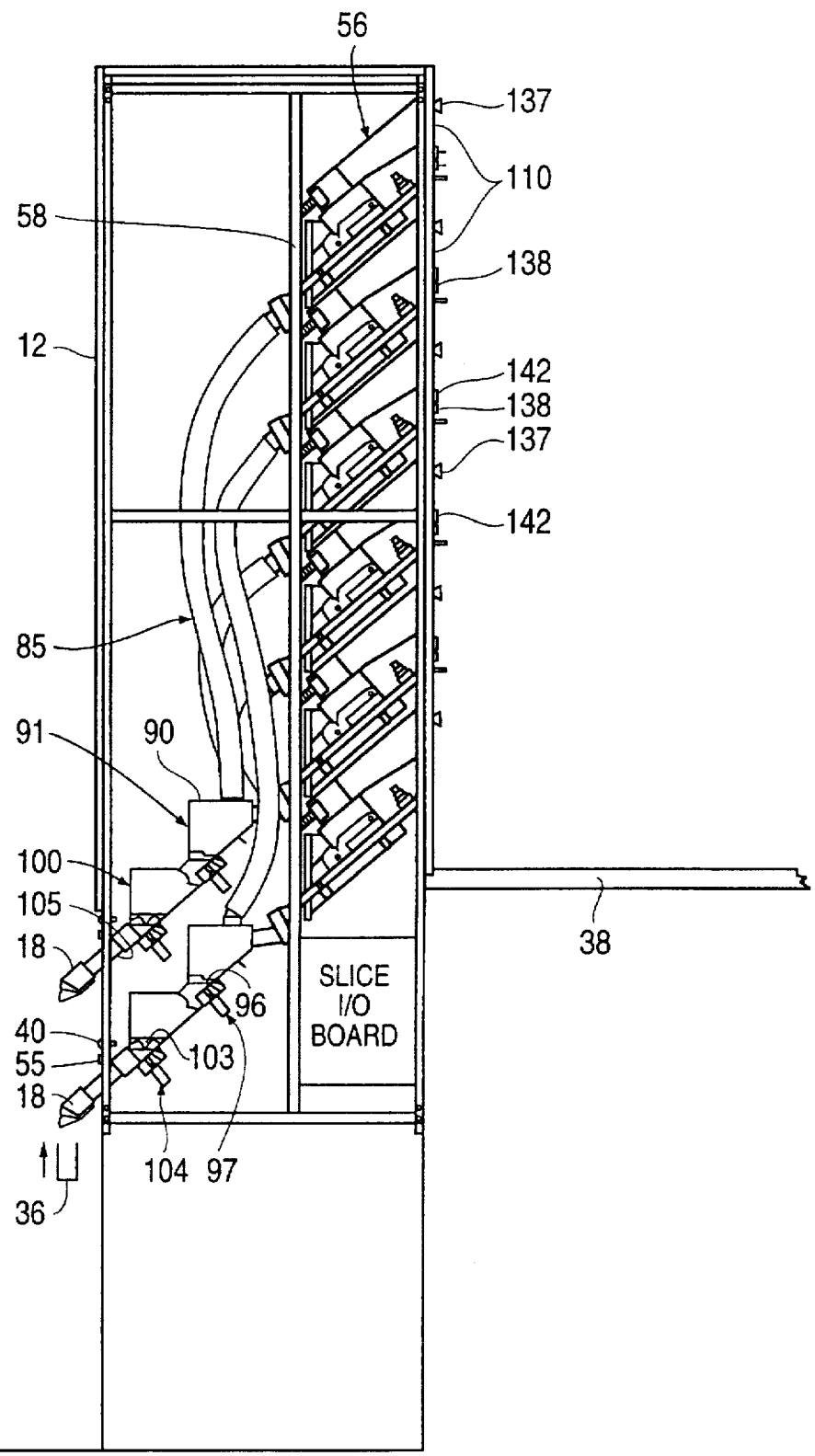
FIG. 3 is an enlarged vertical slice through a cabinet of the drug dispensing system of FIG. 2 showing parts of six drug counting and dispensing subassemblies which comprise one module of the drug dispensing system.
Figure 4:
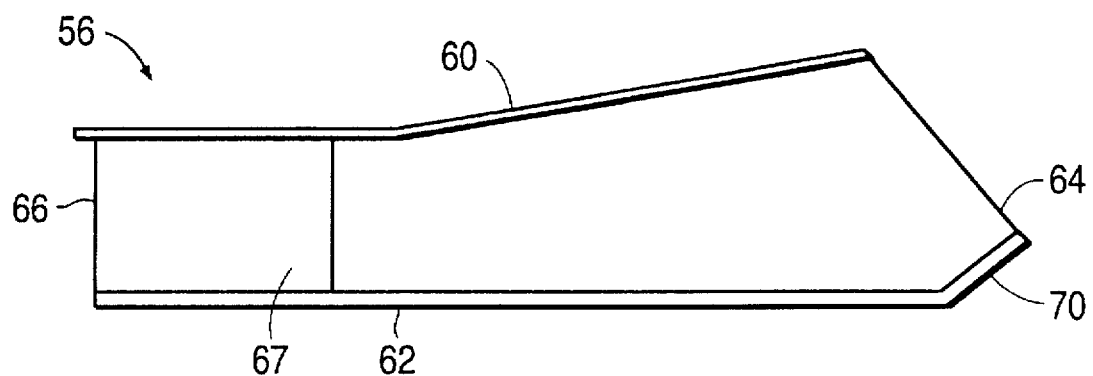
FIG. 4 is a side view of the supply hopper for one the counting and dispensing subassemblies.
Figure 5:
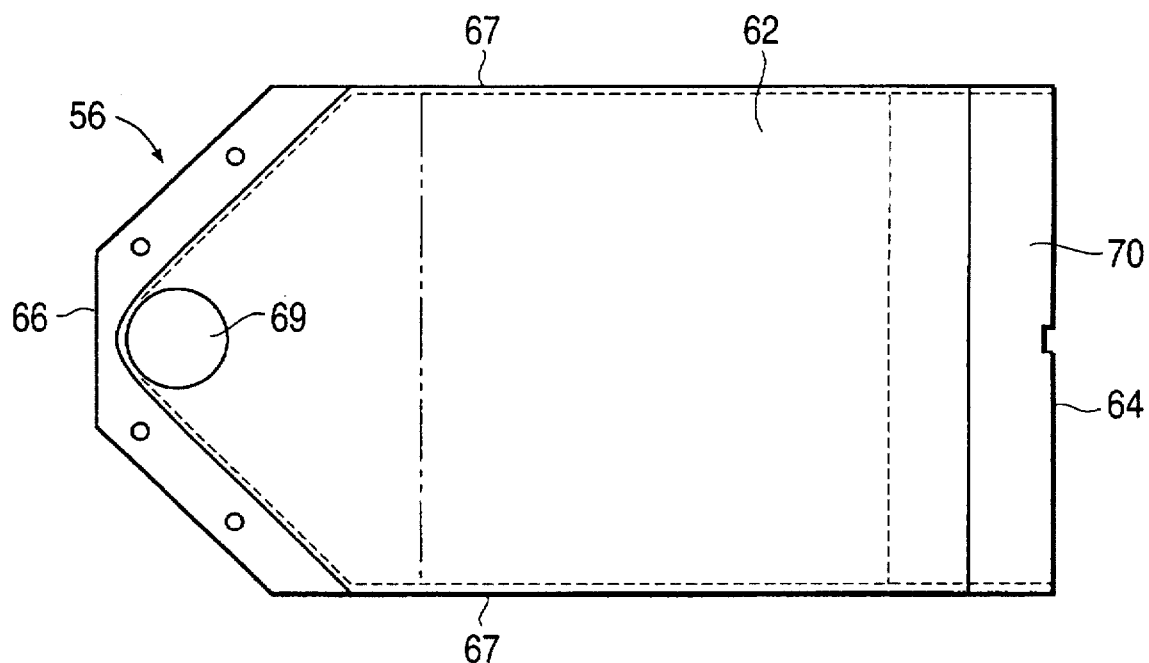
FIG. 5 is a bottom plan view of the supply hopper of FIG. 4.

An outlet tube 84 projects from the counting and dispensing cell 58 through the front panel 82 for connection to a drop tube 85 (FIG. 3). Guide rails 86 are mounted parallel to one another along opposite sides of the counting and dispensing cell 58 between the rear panel 80 and the front panel 82 so that the assembly of the supply hopper 56 and the counting and dispensing cell 58 can be slid from an operative position of the assembly, in which the rear panel 80 is flush with the rear wall of the cabinet 12, to an inoperative, extended position, in which the supply hopper 56 can be detached from the counting and dispensing cell 58, and the counting and dispensing cell can be removed for repair and/or replacement. A limit switch 87 is mounted on one of the guide rails 86 adjacent to the rear panel 80 for actuation when the assembly of the supply hopper 56 and the counting and dispensing cell 58 is in the operative position. Upon the actuation of the limit switch 87, a signal is sent to the control system for the enhanced drug dispensing system according to the present invention. A holdout latch 88 is arranged on one or both of the guide rails so that the assembly can be retained in its extended, inoperative position.

Figure 7:
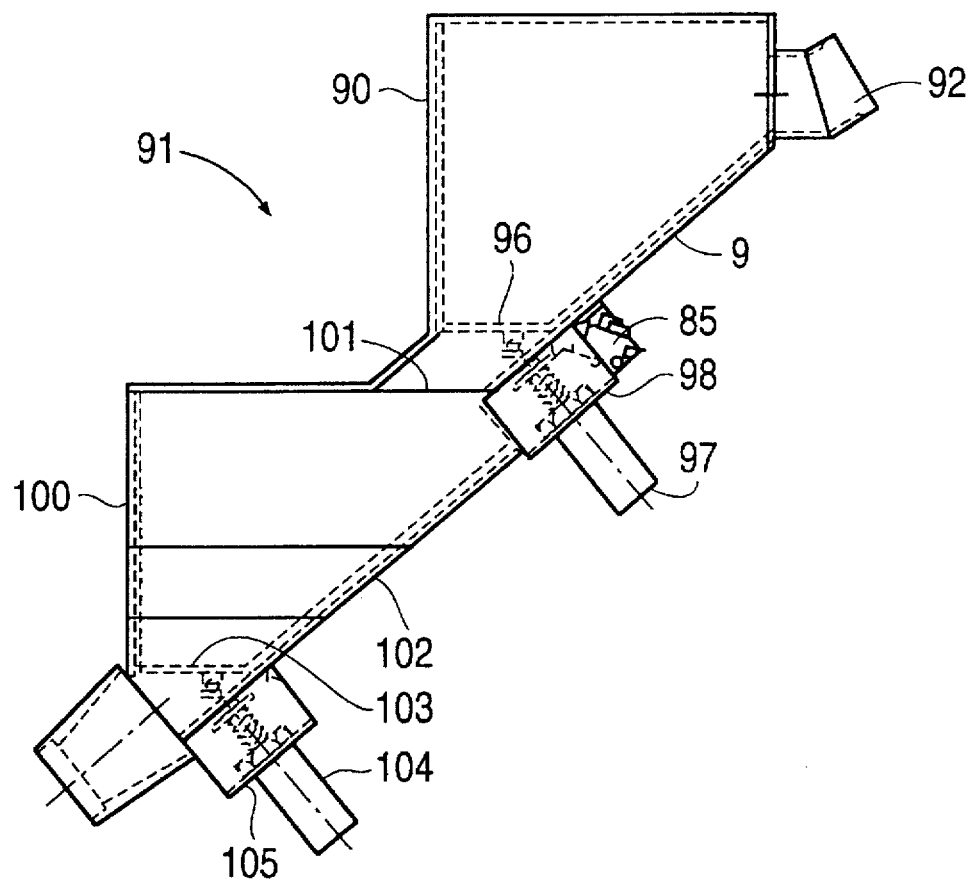
FIG. 7 is an enlarged side view of the buffer assembly of FIG. 4.

Upon a command from the dispensing control system, the counting and dispensing cell 58 counts a desired number of pills and advances them in the dispensing subsystem 14. As can be appreciated from FIGS. 3 and 7, in the present invention the counted pills are advanced through the drop tube 85 to an upper hopper 90 of a buffer assembly 91, which is positioned inside the cabinet 12. The upper hopper 90 has an inlet 92 at or near its upper end to receive the pills from the counting and dispensing cell 58. The upper hopper 90 has a sloped bottom 93 to direct pills to an outlet having a trap door 96. The trap door 96 is hinged to the sloped bottom 93 and is pivotable from a position closing the outlet of the upper hopper 90 to a position in which the outlet is open to allow the pills to pass through the outlet. The pivoting of the trap door 96 of the outlet is controlled by a solenoid 97 connected to the trap door 96 and mounted on a bracket 98 secured to the upper hopper 90. A micro switch 85 senses the open or closed position of trap door 96.

The outlet of the upper hopper 90 of the buffer assembly 91 feeds an inlet of a lower hopper 100 of the buffer assembly. The lower hopper 100 is similar in size and shape to the upper hopper 90 and has an inlet opening 101 at or near its upper end to receive pills from the outlet of the upper hopper 90. The lower hopper 100 has a sloped bottom 102 to direct pills to an outlet controlled by a trap door 103. The trap door 103 is pivotable between a closed position preventing the movement of pills through the outlet and an open position permitting pills to fall through the outlet. Movement of the trap door 103 is controlled by a solenoid 104 mounted on a bracket 105 and connected to the trap door in a manner similar to the solenoid 97 of the upper hopper 90.

Figure 8:
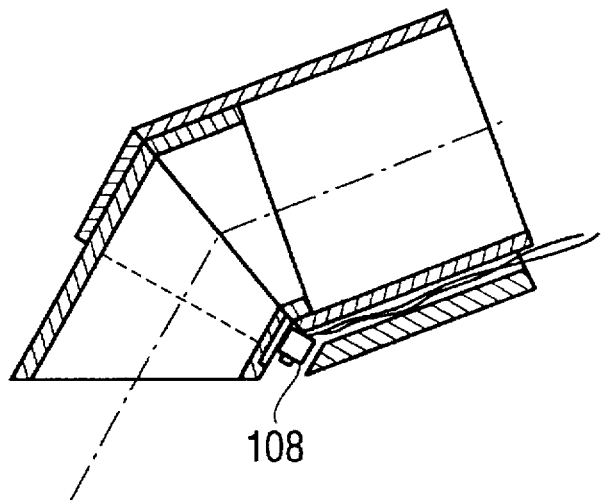
FIG. 8 is an enlarged view of the dispensing snout of FIG. 3.

The pills released from the lower hopper 100 of the buffer assembly 91 fall through a tube 105 (FIG. 3) to the dispensing snout 18 projecting through the front wall of the cabinet 12. As shown in FIG. 8, the dispensing snout 18 has mounted thereon a microswitch 108 which is actuated by placing a pill receptacle under the snout 18 in engagement with the microswitch actuator. The actuation of the microswitch 108, combined with computer agreement that the correct dispensing snout is being selected by the operator, will cause energization of the solenoid 104 controlling the trap door 103 of the lower hopper 100 of the buffer assembly 91, so that the trap door is opened, allowing the pills in the lower hopper to fall through the tube 105 and the snout 18. The operator engages the actuator of the microswitch 108 with an appropriate receptacle 36 for the prescription and actuates the microswitch 108. In addition to causing release of pills from the lower hopper 100, the actuation of the switch 108 sends a signal to the control system that dispensing from the snout 18 is complete. It is preferred that the supply hopper 56, the buffer assembly 91, the tube 105, and the snout 18 be made of transparent polycarbonate material.

Figure 9:
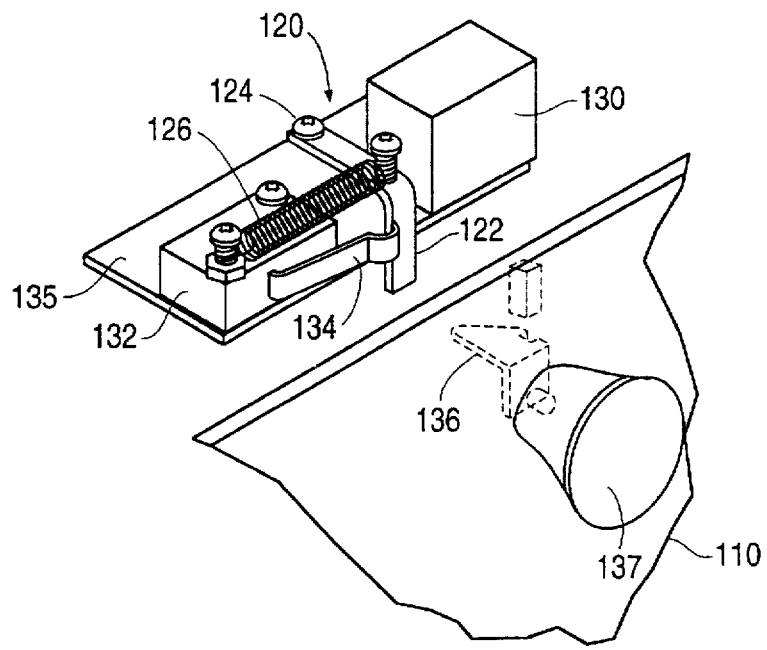
FIG. 9 is a perspective view of a latching mechanism for a supply hopper security door.
Figure 10:
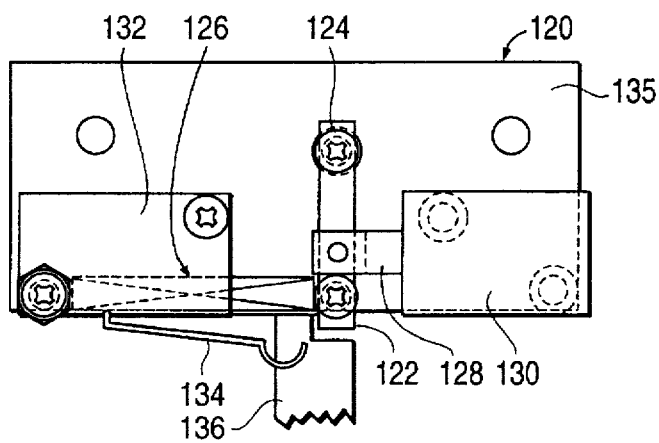
FIG. 10 is a top plan view of the latching mechanism of FIG. 10.
Figure 11:
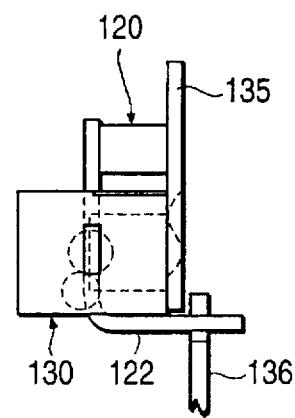
FIG. 11 is a right end view of the latching mechanism of FIG. 11.
Figure 12:
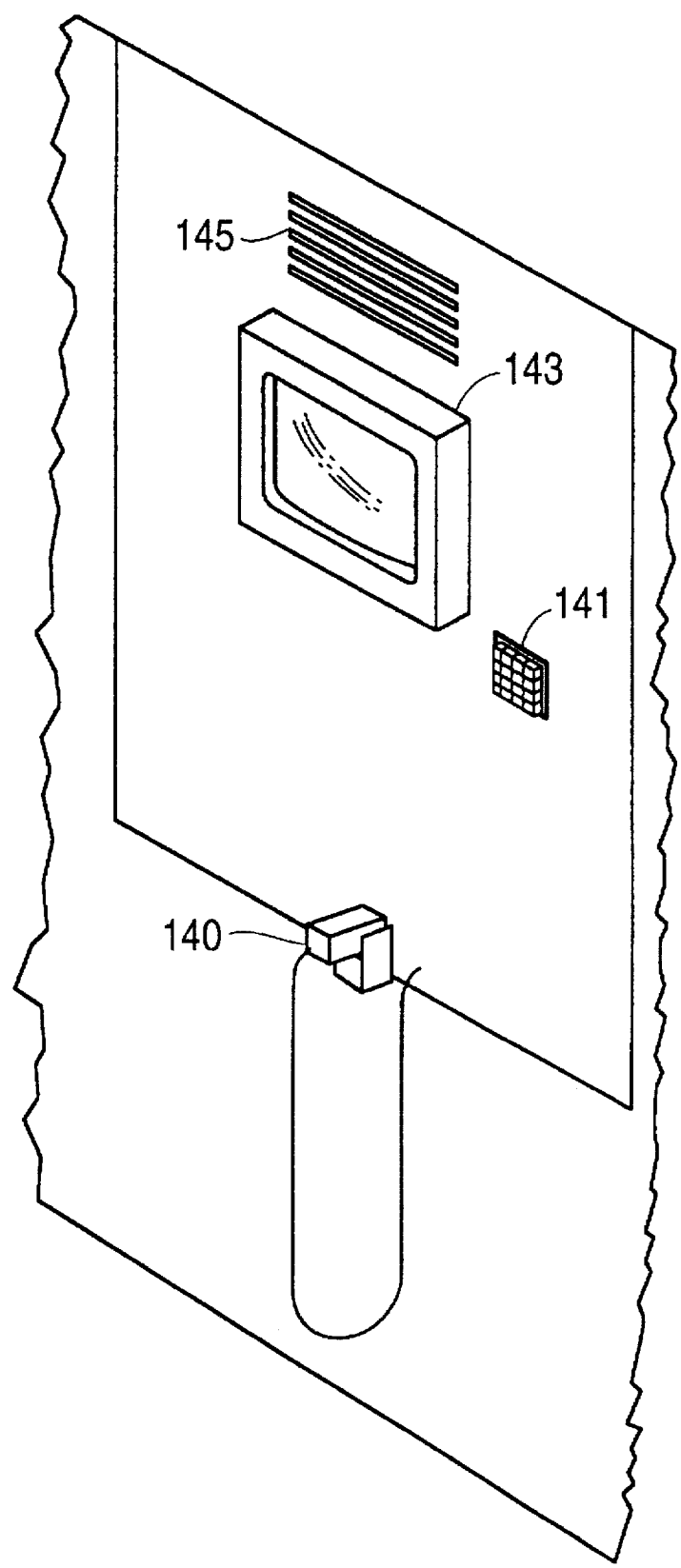
FIG. 12 illustrates a console on the back side of the dispensing array to be used by the refill operator.

The inlet 16 for each of the dispensing subsystems 14 is defined by a opening in a rear wall of the cabinet 12. A security door 110 (FIG. 3) is hinged to the rear wall of the cabinet 12 at the bottom of the opening defining the inlet 16 and is pivotable between a closed position, in which the door covers the opening and prevents access to the inlet 16, and an open position, in which the door uncovers the opening and provides access to the inlet. A latching mechanism 120 is provided at the security door 110 to lock the door in its closed position and, thereby, prevent access to the associated dispensing subsystem 14. As can be seen from FIGS. 9–11, the latching mechanism 120 includes an L-shaped pivot arm 122 mounted for movement in a short arc about a pivot member 124. A tension spring 126 is connected to the pivot arm 122 to bias the arm to one end of the arc defining the travel of the arm. In this position, the pivot arm 122 locks the security door 110. A movable element 128 of a solenoid 130 is connected to the pivot arm 122 and, when actuated, overcomes the force of the spring 126 to move the pivot arm to the opposite end of its arc for unlocking the security door 110. A limit switch 132 is positioned adjacent the latching mechanism 120 where a control arm 134 for the switch is engaged by the security door 110 when the door is in its closed position. The switch 132 is electrically connected to the control system to signal the open or closed state of the security door 110. The various elements of the latching mechanism 120 are mounted on a bracket 135 which can be secured to the cabinet 12. The pivot arm 122 engages a lock catch 136 secured to the security door 110 in order to hold the door locked closed when the pivot arm is in its locking position. A knob 137 is provided on the security door 110. It is preferred that the security door 110 employ a hinge arrangement which limits the travel of the door so that, in its fully open position, the door 110 slopes from its free edge down to its hinged edge and thereby defines a guide to direct pills through the opening 16 of the dispensing subassembly 14.

Figure 13:
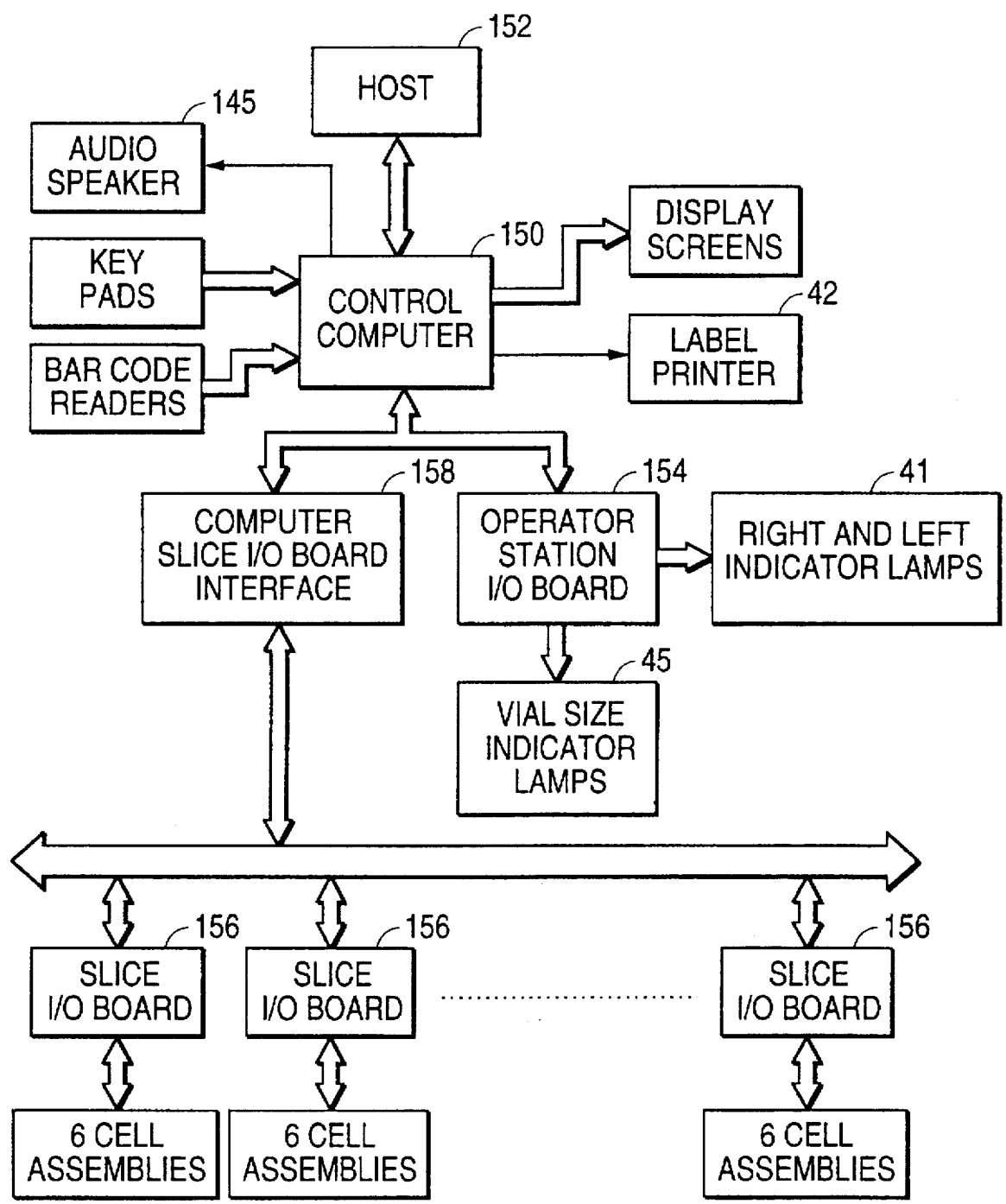
FIG. 13 is a block diagram of the control system of the drug dispensing system according to the present invention.

A refiller console is provided at the back side of the dispensing system array opposite the dispensing operators front console as shown in FIG. 13. The refiller console comprises a bar code scanner 140, which may be of a hand held type, a key pad 141 and a display screen 143. The display screen 144 displays messages to the refill operator.

The computer of the control system keeps track of the quality of pills in the hopper of each cell. In addition, a sensor is provided in the hopper of each cell to detect when the pill quantity is low. When the pill quantity is low, the control computer of the system will direct a synthesized voice message through speaker 145 on the back console to advise the refill technician that a refill of the hopper is needed.

The bar-code reader 140 is used to scan the refill operator's personal identification badge to log in the refill operator and enable refill operations to be carried out. The bar code reading is also used to scan the bar codes on the labels of the drug containers 68 from the factories. In response to the scanning of the bar code or the label of a container, the solenoid 130 of the appropriate security door 110 is actuated to unlock the security door and to provide access to the dispensing subassembly 14 which the door protects. All of the other security doors 110 remain locked. At the same time, a refill indicator lamp 138 adjacent to the appropriate security door 110 lights to indicate the door to be opened for replenishment from the scanned bulk supply container 68.

A transparent pill sample case 142 (FIG. 3) similar to the pill sample cases 55 on the front wall of the cabinet 12 are provided adjacent to each of the indicator lamps 138. A sample pill is placed in each of the pill sample cases to serve a check that the pills being poured into the supply hoppers 56 from the bulk supply containers 68 are the pills which should be poured into the supply hopper. A handle is provided on each of the rear panels so that the assemblies of supply hoppers 56 and counting and dispensing devices 58 can be pulled out of the cabinet 12 from their operative positions to their extended, inoperative positions. The assemblies are locked in place and can only be removed under control the computer system by an authorized technician. Access panels are also provided in the rear wall of the cabinet 12, below the platform 38, to provide access to each of the slice I/O boards.

In operation, using the bar-code scanner and employee badge, the operator logs into a computer embodying the control system. A prescription label for the next prescription to be filled is printed by the label printer 42 on a command from the control system. The indicator lamp 45 associated with the bin 44 holding the appropriate receptacle 36 flashes. The operator places the label on the receptacle 36 and verifies to the control system the bar code on the label by using the hands-free bar code reader 46. The indicator lamp 41 associated with either the left side or the right side of the operator workstation flashes to indicate the general area where the next order will be delivered. The indicator lamp 40 associated with the particular dispensing snout 18 where the order will be delivered also flashes. The operator fills the order by engaging the indicated snout 18 with the receptacle 36. The dispensing system 10 will not release drugs into the receptacle 36 without bar code verification by the bar code reader 46, thus assuring that the proper drugs go into the proper receptacles. The operator puts cotton into the receptacle 36 and a cap onto the receptacle and places the receptacle in the delivery chute 30. The sensor 37 at the inlet 32 of the delivery chute 30 detects the placement of the receptacle 36 in the chute and sends a signal to the control system, which turns the indicator lamp 40 at the dispensing snout 18 off. The signal also indicates to the control system that the lower hopper 86 of the buffer assembly 74 is ready to receive pills for another prescription. It is contemplated that the operator station can include the dispensing snouts 18 of a large plurality of subassemblies 14 in increments of six dispensing snouts associated with one slice or module 19, and that any number of dispensing subassemblies can be provided at one workstation, all have dispensing snouts at a convenient dispensing height.

Another person at the backside of the cabinet 12, after logging in by means of the bar code reader, fills the hoppers 56 supplying the counting and dispensing cells 58. The filling is done independently of the dispensing operation and without interfering with the dispensing operation. All of the security doors 110 are initially locked. When a counting and dispensing device 58 requires replenishment, the refill operator at the back of the cabinet 12 reads with the scanner 140, the bar-coded label on a bulk supply container 68 of drugs. In response to the reading, the control system causes the indicator lamp 138 to flash adjacent to the security door 110 of the hopper 56 for the counting and dispensing cell 58 used to fill orders for the drug whose container label was scanned. The scanning of the bulk container label also causes the release of the lock 120 of the appropriate security door 110 so that access to the supply hopper 56 protected by the door is permitted. After the supply hopper 56 is filled, the security door 110 is closed, whereupon it locks automatically. Unless the security door 110 is closed, all of the other security doors remain locked, and access to any other supply hopper 56 is prevented. In case of a malfunction of any of the counting and dispensing cells 58, the malfunctioning cell is removed through the back wall of the cabinet 12 and replaced with a spare cell. The removed cell can be repaired without interrupting the dispensing operation.

Upon a command from the dispensing control system, the appropriate counting and dispensing cell 58 counts a desired number of pills and advances them to the buffer assembly 91. The solenoid-operated trap door 96 controlling the outlet of the buffer assembly upper hopper 90 opens, releasing the pills in the upper hopper. The pills released from the upper hopper 90 are directed to the lower hopper 100. After verification of the prescription number by bar code reader sensing the bar code printed on the prescription label, the solenoid-operated trap door 103 controlling the outlet of the lower hopper 100 opens to release the pills from the lower hopper in response to the presence of the receptacle 36 at the dispensing snout 18, the pills falling from the lower hopper through the tube 105 to the dispensing snout 18. Only that dispensing snout will activate as the computer has disabled all others assuring the operator went to the correct location.

The electronic control system of the invention as shown in FIG. 13 comprises a control computer 150 which is connected with a host computer 152. The host computer 152 on receiving a ready message from the control computer 150 transmits packets of data each representing an individual prescription and containing all of the data of the prescription, including the doctor's name, the patient's name, the drug of the prescription, the number of pills in the prescription, the prescription number, and the identification of the particular dispensing subsystem 14 containing the particular dispensing cell which contains the drug to be dispensed. These individual packets of data are referred to as scripts and are stored in a portion of the internal memory of the control computer 150 set aside to receive the scripts and referred to as the script buffer.

The control computer 150 is programmed to receive signals from the key pads 52 and 141 on the front and back consoles of the system and to receive signals from bar code readers 46 and 140. The control computer 150 also controls the label printer 42 which prints the prescription labels and controls the display screens 54 and 143.

The control computer 150 sends output signals to an operator station I/O board 154 which in response to the signals from the control computer 150 will energize the appropriate one of the vial size indicator lamps 45 and will also energize the appropriate one of the right and left indicator lamps 41 to indicate to the dispensing operator on which side of the array the selected dispensing cell is located.

The computer 150 selects and communicates with a slice I/O board 156 by means of an interface board 158. As explained above, the dispensing cells are arranged into a multiplicity of subgroups called slices each containing six vertically arranged dispensing cells as shown in FIGS. 2 and 3 and each slice of dispensing cells is controlled by a separate slice I/O board 156. Each slice I/O board 156 selects one of six dispensing cells in the corresponding slice to operate and count out pills, controls the dispensing cell to count the correct number of pills, and communicates back with the control computer 150 via the interface board 158 to advise the control computer 150 when the dispensing operation has been completed. Each slice I/O board can act to fill up to six prescriptions at the same time. The slice I/O board controls the energization of the solenoids 97 and 104 to open the trap doors 96 and 103 at the appropriate times for each dispensing cell and also controls the energization of the indicator lamps 40 to indicate which dispensing snout a drug is to be dispensed from. The slice I/O board receives signals indicating the status of the switches 108 each detecting the positioning of a vial at a snout 18 to receive a drug, the status of the switches 85 indicating the open and closed state of the upper hopper trap doors 96, the status of the switches 132 indicating the open and closed state of the security doors 110 and the interlock switches 87 indicating the presence or absence of dispensing cells.

Figure 14:
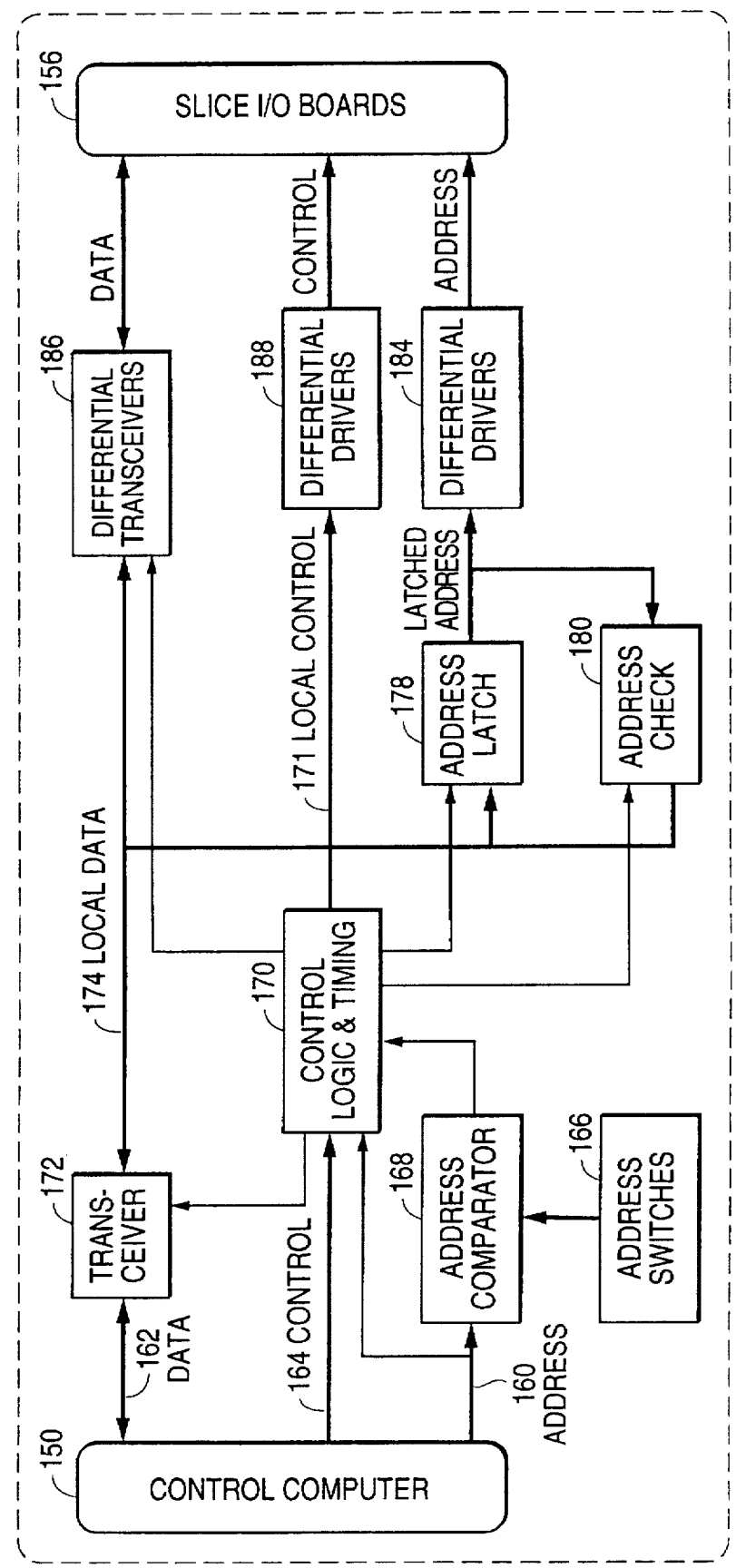
FIG. 14 is a block diagram illustrating the details of a circuit in an interface board forming part of the system shown in FIG. 14.

The block diagram in FIG. 14 illustrates the circuit of the interface board 158 in more detail. As shown in FIG. 14, the interface board 158 connects with the control computer 150 via an address bus 160, a data bus 162 and control signal bus 164. The signals on the address bus 160 are used to select the interface board of FIG. 14 to transmit or receive signals over the data bus 162. If the address signals on the bus 160 match an address represented by address switches 166, this match will be detected by an address comparator 168 and the interface board 158 will be selected. When the address comparator 168 detects a match of the address on the bus 160 with the address switches 166, it signals the occurrence of the match by applying a match signal to control logic and timing circuit 170, which is enabled by the match signal. The signals on the data bus 162 can represent either an address to select a slice I/O board and an output register on the selected slice I/O board or they can be data signals to be stored in a selected register on the slice I/O board. When signals are transmitted from the computer 150 to the interface board over the bus 162, the enabled control logic and timing circuit 170 will enable transceivers 172 to transmit these signals to local data bus 174. When the signals are transmitted on the data bus 162 represent an address, one bit of the address signals on the address bus 160 called an address control bit will indicate this fact and this address control bit is received by the control logic and timing circuit 170. When the address control bit indicates that the signals on the local data bus are address signals the control logic and timing circuit 170 enables the address latch 178 to receive the address signals. When the selected bit of an address bus 160 indicates that the signals on data bus 162 are data signals, the signals are not latched into the address latch 178 and the control logic and timing circuit 170 will produce a write signal on local control bus 171 indicating that the transmitted signals are local data signals.

When the control logic and timing circuit 170 latches signals into the address latch 178, these signals will be applied to an address check register 180 where they will be restored in response to a signal from the control logic and timing circuit 170 and these address signals will be transmitted back over the local data bus 174, the transceiver 172 and the data bus 162 to the computer 150 for a comparison in the computer 150 to insure that the address latched in the address latch 178 matches the address sent to the address latch. The address latched in the address latch 178 is transmitted by differential drivers 184 over an output address bus 191 to each of the slice I/O boards 156. When the signals on the data bus 162 do not represent an address to select a slice I/O board 156, but instead are local data signals, the circuit 170 will enable differential transceivers 186 address so that each of the slice I/O boards may be individually selected by the matching carried out by the address comparator 202. The read and write signals transmitted over output control bus 189 to each of the slice I/O boards 156 are transmitted by differential receivers 208 to the control and logic timing circuit 206. When a write signal is received on the control bus 189, the control and logic timing circuit 206, if enabled by the address comparator 202, will enable an input register location decoder 210 to respond to respond to the three least significant bits in the address signals transmitted from the interface board over address bus 191. In response to the three least significant bits, the input register location detector will select one of seven output registers 211 through 217 or the FIFO register 218 to store received data signals. When the control logic and timing circuit 206 receives a write signal, it will also enable differential transceivers 220 to transmit data signals received over the data bus 187 from the interface board to the output registers 211 through 217 and to the FIFO register 218. Thus, when the signals on the control bus 189 comprise a write signal, one of the registers 211 through 217 or the FIFO register 218 will be enabled to receive and store data signals and data signals received on bus 187 will be stored in the selected register. The data signals received in the output registers 211 through 217 each serves to select one of the six dispensing subsystems 14 in the slice corresponding to the activated slice I/O board 156. The output register 211 controls the solenoids 97 and, accordingly, controls the opening of the trap door 96 at the outlet openings of the upper hoppers 90. Thus, when the output register 211 is selected by the output register location detector 210, data signals will be stored in the register 211 to select one of the six dispensing subsystems 14 in the slice and energize the solenoid 97 in the selected dispensing subsystem. Accordingly, the pills will be dumped from the upper hopper 90 to the lower hopper 100 in the selected subsystem 14. The output register 212 controls the solenoids 104 in the dispensing subsystems 14 in the slice corresponding to the activated slice I/O board 156. Accordingly, when the output register 212 is selected by the location decoder 210 and receives data, it will select and energize a solenoid 104 and release the pills from the lower hopper 100 to pass through the corresponding output snout 18 into a vial. The output register 213 controls the snout indicating lamps 40 for the selected slice. When the output register location detector 210 selects the output register 213, the register 213 receives and stores data signals and the data signals in the register 213 will select and energize a selected snout indicator lamp 40 corresponding to the dispensing cell selected by the data in the output register 213. The output register 214 corresponds to the indicator lamps 138 to indicate the refill door to be opened in the back panel in response to the wanding on the bar code on a bulk package of drugs by the refill operator prior to refilling. Thus, when the output register 214 is selected and receives data, it will select and cause the energization of an indicator lamp 138 adjacent to a refill security door to indicate to the refill operator that the adjacent refill security door is to be opened to access the corresponding supply hopper 56.

The output register 215 controls the solenoids 130 in the selected dispensing subsystem for unlocking the rear refill doors when the output register 215 is selected by the location decoder 210 and receives data. The data in the register 215 will select and energize a solenoid 130 and thus unlock the selected refill door. The registers 216 and 217 are unused in the current preferred embodiment and are provided for future modification of the existing system.

When the location decoder 210 selects the FIFO 218, the data received on the data bus by the differential transceiver 220 will be what is referred as a script packet which contains the cell number of the selected dispensing cell in the slice and also the number of pills to be dispensed. In response to the selection of the FIFO register 218, this script packet will be stored in the FIFO register 218 to be used by a microcontroller 242 in controlling the operation of the selected dispensing cell in a manner described in more detail below.

Depending on the data placed in the registers 211 through 217, the outputs from the registers 211 through 217 can also select vibration drivers. These vibration drivers are used in the case of a dispenser dispensing too slowly or failing to dispense in the manner as described in more detail below.

As described above, each dispensing subsystem has four microswitches which indicate the status of the dispensing subsystem. One microswitch 108 is located at the snout 18 and detects the presence of a vial at the snout 18 to receive pills from a second buffer 86. A second microswitch 85 detects whether 97 has been actuated and has opened the trap door 96 is open or closed. A third microswitch 132 detects that the refill door 110 as shown in FIG. 3 is open or closed. The fourth microswitch 87 is the cell interlock switch and detects whether the dispensing cell is present in the dispensing cell array. With four switches for each dispensing subsystem 14, a slice of six dispensing subsystems has 24 such switches. These 24 switches generate most of the slice status signals, designated in FIG. 13 by reference number 222. In addition to the signals generated by the dispensing subsystem microswitches, the slice status signals 222 also include the signals generated by the low level sensors in the hoppers of the dispensing cells. The slice status signals 222 are applied to input registers 231 to 234. When the control logic and timing circuit 206 receives a read signal through the differential receiver 208 over the local control signal bus 189 from the interface board 158 and the slice I/O board has been selected as detected by the address compare circuit 202, the control logic and timing circuit 206 will enable an input register location decoder 236 to respond to the three least significant bits on address bus. In response to these three bits, the input register location decoder 236 may select one of the input registers 231 through 234 to apply output signals representing eight of the slice status signals 222 through the differential receiver 220 over the data bus to the I/O interface board 158 and from the I/O board interface 158 to the control computer 150. In this manner, the computer 150 can read out and obtain the status of the 24 switches and the six hopper level sensors in a selected slice of six dispensing subsystems 14.

As described with reference to FIG. 2, each time the operator filling prescriptions has filled a vial, he places it in the chute 32 and the placing of a vial in the chute 32 is detected by a photodetector 37 which generates a chute signal indicating that vial has been deposited in the chute 32. The chute signal generated by the photodetector 37 is applied to one of the slice I/O boards 156, in which the chute signal is temporarily stored in a chute sensor interface 238. The stored chute signal is applied to the input register 234 where it will be read out to the computer 150 through the I/O board interface 158 when the register 234 is selected to read out by the input register location detector 236. The chute sensor interface 238 is reset upon the stored chute signal being read out.

Figure 15A:
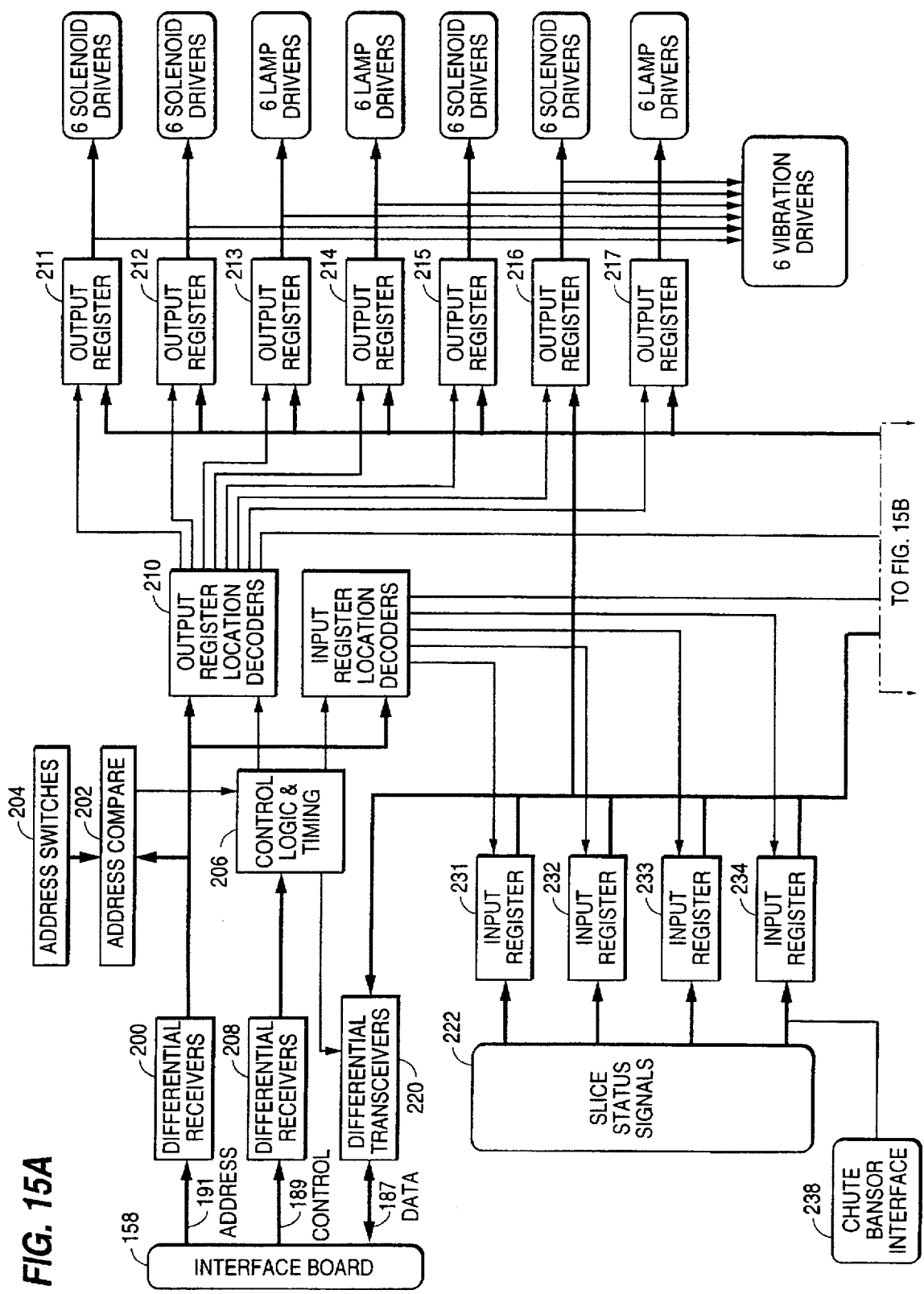
FIGS. 15A and 15B show a block diagram of a circuit on an input/output board forming part of the system of FIG. 14.
Figure 15B:
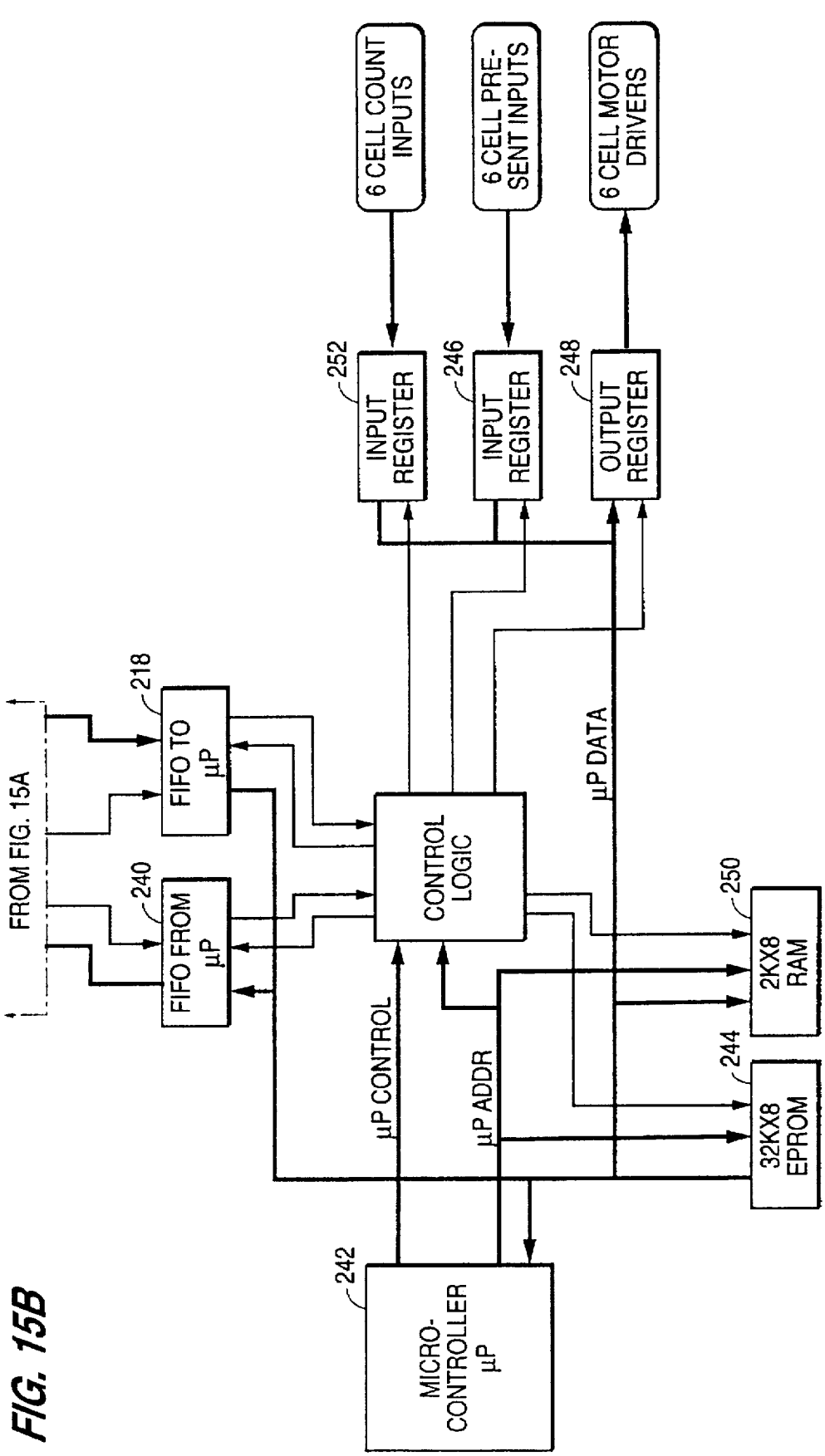

The slice I/O board, as shown in FIG. 15B, also has an input FIFO 240 and the output FIFO 240 can be selected by the input register location decoder 236 for readout. When a read signal is received over the control bus through the differential receivers 208 by the control and timing logic 206 and the input registration location decoder 236 selects the input FIFO 240 in response to the address signals received through the differential receivers 200 over the address bus 191 from the interface board 158, the data in the FIFO 240 will be read out through the differential transceivers 220 and through the interface board 158 to the computer 150.

Each slice I/O board, as shown in FIG. 15B, contains a microcontroller 242 which responds to the script packets stored in the FIFO 218 and stores status packets in the FIFO 240 to provide data to the computer 150 representing the current status of any prescription being filled in the slice. The microcontroller 242 operates under the control of a program stored in EPROM 244 and employs control logic 245 to route data between a random access memory 250 and the FIFOs 218 and 240 and also to output register 248 and from input registers 246 and 252. When a script packet has been stored in the FIFO register 218, the microprocessor 242 will read out this packet of data and process it by first storing a bit in the output register 248 corresponding to the cell selected by the script packet of data and when this bit is stored in the output register 248, the cell motor driver will energize the motor to drive the selected dispensing cell. The microprocessor 242 will also store the script packet in the random access memory 250. As the motor operates and is energized to dispense pills, the actuated cell will produce output pulses each time a pill is dispensed and these pulses are received in input register 252 and counted in the random access memory 250 by the microcontroller 242. When the number of pills dispensed as determined by this count registered in the RAM 250 equals the count in the script packet, the microprocessor 242 stops the cell motor by changing the corresponding bit in the register 248 so that the cell motor is de-energized and stops dispensing pills. If the cell motor does not draw current in response to power applied from the corresponding cell motor driver, the cell operating generates an output signal indicative of this fact and this output is stored in the corresponding bit position of the register 246 to indicate that the dispensing cell is not available.

In addition, each time a script packet is stored in the FIFO 218, the microprocessor 242 will store a status packet in the FIFO 240 containing the number of the dispensing cell which has been selected by an incoming script packet stored in the input FIFO 218 and a character representing the present status of the prescription represented in the corresponding script packet. The status of the prescription may be indicated as F meaning that the cell is filling the prescription, W meaning that the cell is filling the prescription with a slow delivery, G meaning that the filling of the prescription has been completed, H meaning that the cell for the prescription is not available, A meaning that the cell is busy filling a prescription in response to a prior script packet received by the FIFO 218, and X meaning that the dispensing cell microswitch, which generates a pulse as each pill is dispensed to enable the dispensed pill to be counted, is stuck. The microcontroller determines the status of the prescription of the script packet and then sets the character representing the status in the corresponding status packet in the input FIFO 240. The microcontroller determines that the cell is not available by checking the input register 246 and determines that a cell is busy by determining that the cell selected by the script packet is in the process of filling a prescription represented in a previously received script packet in the FIFO 218. The status conditions indicated by characters A and H should not occur, but should they occur through malfunction, the microcontroller stores the corresponding character in the corresponding status packet in input FIFO 240. If the cell selected by the script packet is present and is not busy, the microcontroller sets the character F in the status packet to indicate that the prescription is being filled. The microcontroller compares the rate of pulses representing counts received back from the counter with a timer and if the pulse rate is below a predetermined minimum, then it sets a character W in the corresponding status packet to indicate that the cell is slow in dispensing the pills. If the microcontroller receives no pulses from an energized cell within a preselected time period, the microcontroller sets the character X in the corresponding status packet to indicate that the dispensing cell has a stuck microswitch. When the dispensing cell has completed dispensing the selected number of pills, as indicated by the count of the number of pills registered in the random access memory 250 equalling the pill count provided in the script packet in the FIFO 218, the microcontroller sets the character G in the corresponding status packet in the FIFO 240. When the script register location detector 236 selects the input FIFO 240, the cell status packets stored in the input FIFO 240 will be read out and transmitted to the computer 150.

Figure 16:
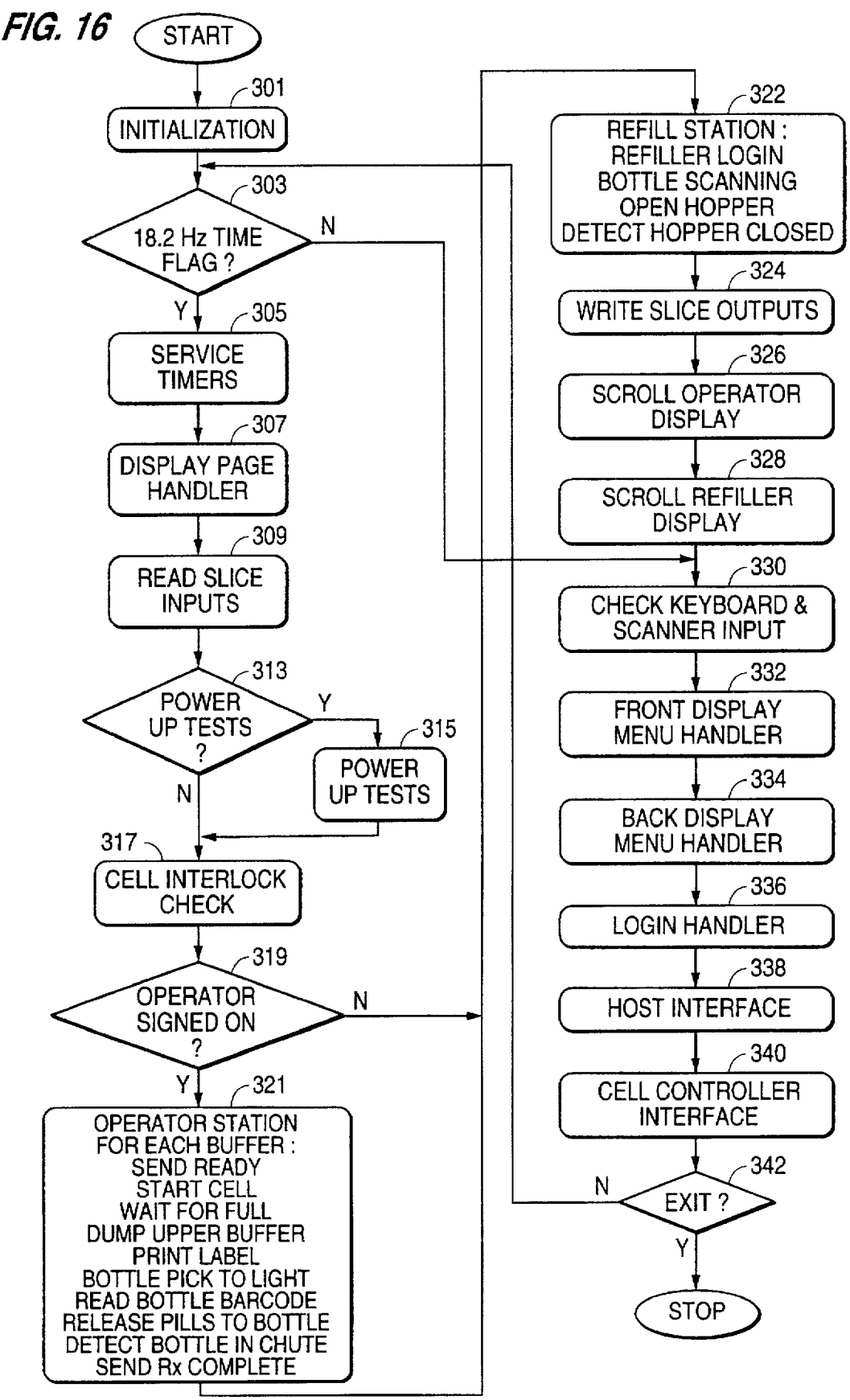
FIG. 16 is a flow diagram showing the operation of the control system.

The program by which the computer 158 controls operation of the dispensing system is represented by the flowchart shown in FIG. 16. A source code listing of the program in "C" is submitted herewith as an appendix to the application.

As shown in the flowchart, the program upon being started enters into an initialization routine 301 in which the constants and variables are set to their initial values whereupon the routine enters into a decision sequence 303 to determine whether a 18.2 hertz timer has timed out. If the timer has timed out, the program enters into the control sequence of the program and if the timer has not timed out, the control sequence of the program is skipped. Accordingly, the program will sequence through the control sequence of the program about every 0.05 seconds. Upon entering the control sequence of the program, the program first enters into a routine 305 wherein each of the timers used in the control sequence are incremented and then the program enters into routine 307 in which the program sets up and controls the display on the front display screen 54 and also the display on the refill operator's display screen 143 on the back side of the array for the refill operator.

Following the display handler routine 307, the program enters the routine 309 to read the slice inputs from all of the slice I/O boards 156 in the system. It is during this routine that the computer receives the data from the input registers 231 through 234 on each slice I/O board. Following the routine 309, the program enters into the decision sequence 311 in which the program determines whether or not a power up test is to be performed. The program is designed to have a maintenance technician to log into the system to start up the system or for maintenance purposes. During start-up, the power up test is performed. In the power up test, the status of the switches in each of the I/O boards is checked and the output pill hoppers 90 and 100 are flushed of any stray pills left in these hoppers. After start-up, during normal on-going operation, the power-up test is skipped and the program proceeds directly into the next routine of the control sequence, which is the cell interlock test. In this routine, the program checks the open or closed status of the cell interlock switches 87, which are closed when the dispensing subsystems are present in the dispensing array from the data received from the slice I/O boards in routine 309. The routine 317 displays a message on the display screens indicating which cells are not present. Following the cell interlock check routine 317, the program enters the decision sequence 319 wherein the program determines whether or not the prescription dispensing operator has logged in. If the prescription dispensing operator has not logged in, the program returns to the decision sequence 303.

If the dispensing operator has logged on, the program enters into the operator station routine 321 in which the major control functions of the dispensing operation of the dispensing system are carried out. These functions include selecting a selected dispensing subsystem 14 in response to a received prescription and causing the cell motor of the dispensing cell 58 in the selected subsystem to be energized to cause it to begin dispensing pills into an upper hopper 90, printing prescription labels from each received prescription in turn, energizing the solenoid 97 to dump the pills from the upper hopper 90 to the lower hopper 100, to energize the solenoid 104 to release the pills from the lower hopper 100 to the output snout 18 to be received by a pill bottle or vial. In addition, the operator station routine 321 also controls the energization of the right and left side indicator lamps to indicate which side of the array the prescription is to be dispensed from and controls energization of the snout indicator lamps 40 to indicate from which snout a prescription ready to be released is to be dispensed. In addition, the operator station routine controls the energization of the bin indicator lamps 45 to indicate from which bin the vial is to be obtained for the prescription being filled.

After completing the operator station routine 321, the program proceeds into the refill station routine 322 wherein the program causes the appropriate functions to be carried out with respect to the refill operation carried out on the back side of the array of dispensing subsystems 14. Specifically, the refill routine checks to determine that the refill operator has logged in and then responds to the data received from wanding of the bar code on refill cartons to unlock the security door 110 of the corresponding dispensing subassembly 14 so that the refill operator can open the unlocked door and dump the drugs into the supply hopper 56 of the appropriate dispensing subassembly. Before unlocking the selected door, the routine first determines whether all the security doors are closed. The selected door will not be unlocked unless all doors are closed. In this routine, the program also controls the energization of the appropriate signal lamp to indicate to the refill operator which door has been unlocked in response to the scanning of the bar code on the refill carton. The program maintains a count of the number of pills in the input hopper of each dispensing cell. This count is called the hopper quantity. As part of the refill station routine, this hopper quantity is updated by adding the number of pills supplied in the refill operation to the hopper quantity. This hopper quantity is used by the computer to determine when the quantity of pills in a dispensing subsystem supply hopper is low and needs refilling. As stated above, the control system also includes a low level sensor in each hopper to indicate when the pill quantity in a given hopper is low.

Following the routine 322, the program enters into the write slice outputs routine 324 in which the computer 150 performs the function of transmitting the data to the registers 211 through 217 to complete the functions of energization of the selected solenoid drivers and the selected lamp drivers. Following the write slice output routine 324, the program proceeds through routines 326 and 328 to service the scroll of the display on the front display screen 54 and to perform a similar function for the display screen 143 for the refill operator. After the routines 326 and 328 have been completed, the program will have completed each of the routines and functions of the control sequence, which are performed once every 20th of a second, that is, every time the 18.2 hertz time flag has timed out when the program enters the decision sequence 303.

If in decision sequence 303, the time flag is not timed out, the program skips the control sequence to enter the routine 330 and it will also enter the routine 330 after performing the scroll display routine 328. Thus, the control sequence comprising routines 305, 307, 309, 317, 319, 321, 322, 324, 326 and 328 are performed about once every 20th of a second. The routine 330 and the routines following this routine in the flow chart are performed at a much higher frequency.

In the routine 330, the program receives the key pad input signals and also the bar code reader input signals. Following the routine 330, the program enters into routine 332 wherein the program carries out the front menu display control function when this control function is called for in response to keyboard input signals from key pad 52. Following the routine 332, the program enters into the routine 334 wherein the program controls the menu display on the refiller display screen when this menu display is called for by key pad input signals.

Following the routine 334, the program enters into routine 336 wherein the program handles any log in by the operator or the technician at the front keyboard 52 as well as any log in by the refill operator at a key pad on the back side of the dispensing array. Following the log in handler routine, the program proceeds into the host interface routine 338 in which the program transmits a ready signal to the host computer and receives new scripts from the host computer in response to the ready signal. Following the routine 338, the program enters into the cell control interface routine 340 in which the computer receives the characters representing the status of each prescription which is the subject of the script packet sent to the output FIFO 218 to start the prescription filling process. As described above, this status information is received from the status packets in the input FIFO 240 and is in the form of letter characters A, F, W, G, H, and X, wherein A means that dispensing cell is busy filling a prescription under the control of a previous script packet in the output FIFO 218, F means that the prescription is in the process of having the pills dispensed, W meaning that the cell is counting out the pills, but the counting process is too slow, G meaning that the filling process of the prescription has been completed, H means the dispensing cell is not present, and X means that the counting microswitch of the dispensing cell is stuck. The computer 150 responds to the received characters in the routine 321 as described in more detail with reference to FIG. 17a through 17d.

Following the routine 340, the program enters into the exit decision sequence 342, from which the program returns again to the timer decision sequence 303, unless an exit has been called for. If an exit has been called for in response to a entry of a command by a technician, then the program will exit the program and the program will end. Upon returning to the decision sequence 303, the program again determines whether the 18.2 hertz timer has timed out and the process repeats.

The system is designed to act on five different prescriptions essentially simultaneously doing different parts of the functions required for the different prescriptions at the same time. One prescription may be in the process of being started to commence counting out pills. Additional prescriptions may be in the process of being counted and dispensed into the respective upper hoppers. Another prescription may be having the pills dumped from the upper hopper to the lower hopper, a fourth prescription may be having its label printed or having its pills released from the lower hopper into a vial. The way that this simultaneous dispensing is accomplished is by having each script containing the information for a prescription to be dispensed stored in a different one of five buffer registers assigned to this purpose. This set of buffer registers is called the script buffer. The status characters A, F, W, G, H, and X representing the current status of these prescriptions are received and stored in the corresponding script buffer register in routine 340.

In successive iterations through operator station routine 321, the computer 150 performs sequential steps of the dispensing process, from starting the pill counting by the dispensing cell to releasing the pills from the lower hopper into the vial, for each script in the script buffer. Each time the computer 150 iterates through the routine 321 every ½0th of a second, a portion of the dispensing sequence is effected for each of the five scripts. In this manner, five scripts stored in the script buffer can be processed essentially simultaneously. The operator station routine 321 is a case variable switching routine wherein the particular function performed for each script buffer during each iteration through the routine depends upon the case variable or status word which may be READY, PRESTART, START, STARTED, FILLING, FULL, DUMPING, LABELWAIT, LABEL, SNOUTWAIT, RELEASE, and CHUTEWAIT. The program changes the status word in the above listed sequence as a given script is being processed unless a malfunction occurs, in which case the stats word is changed to CANCEL.

Figure 17A:
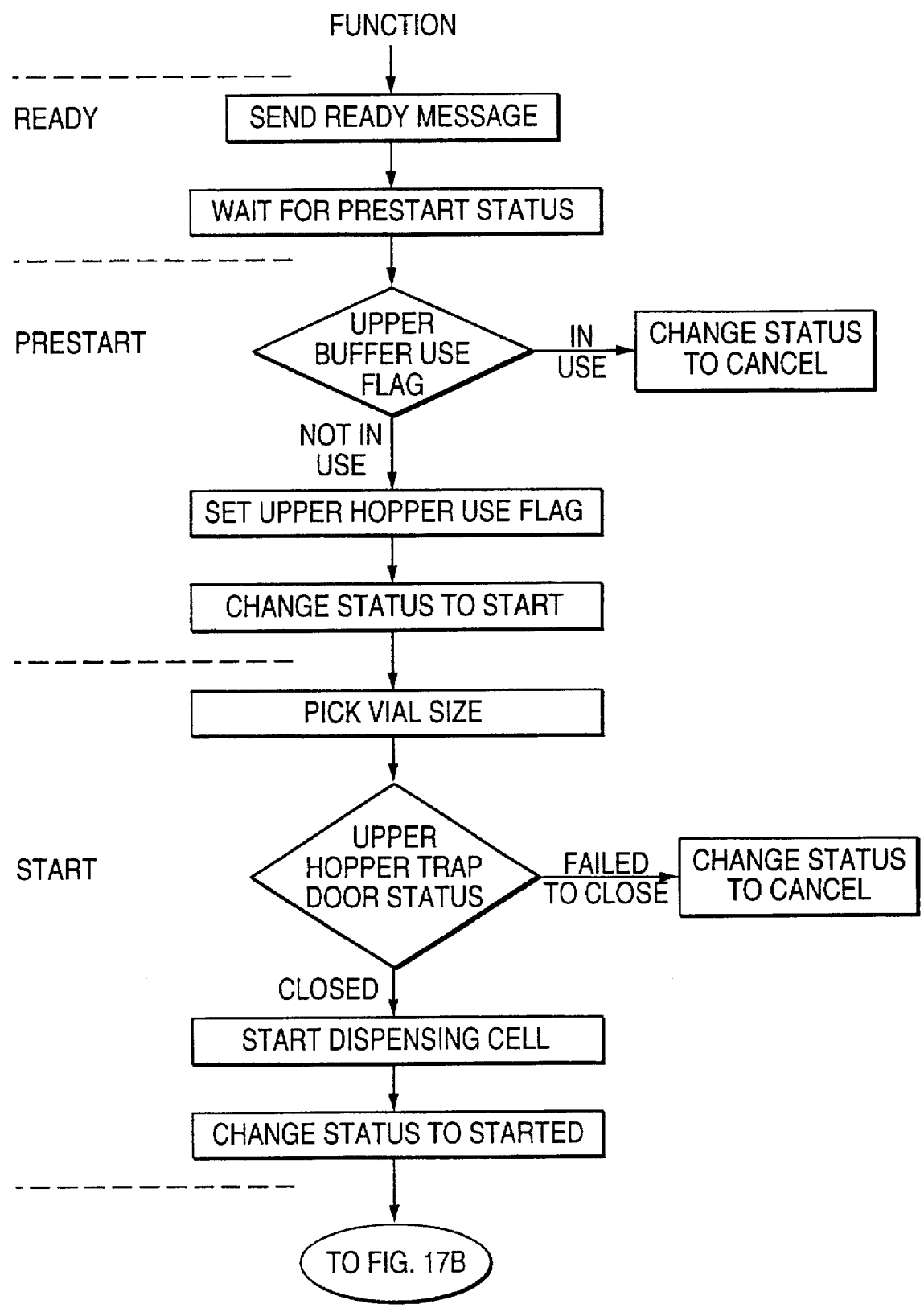
Figure 17B:
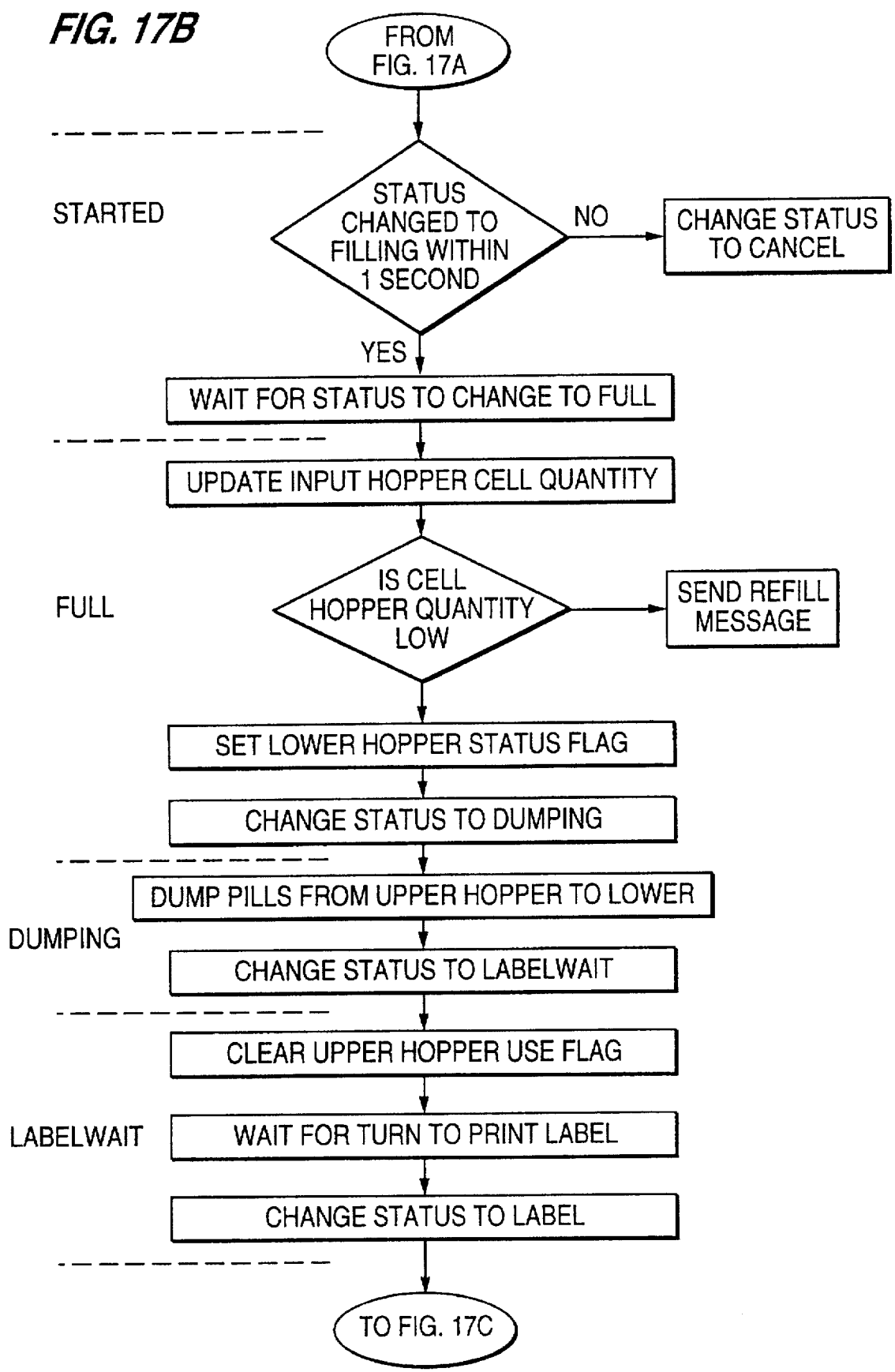
Figure 17C:
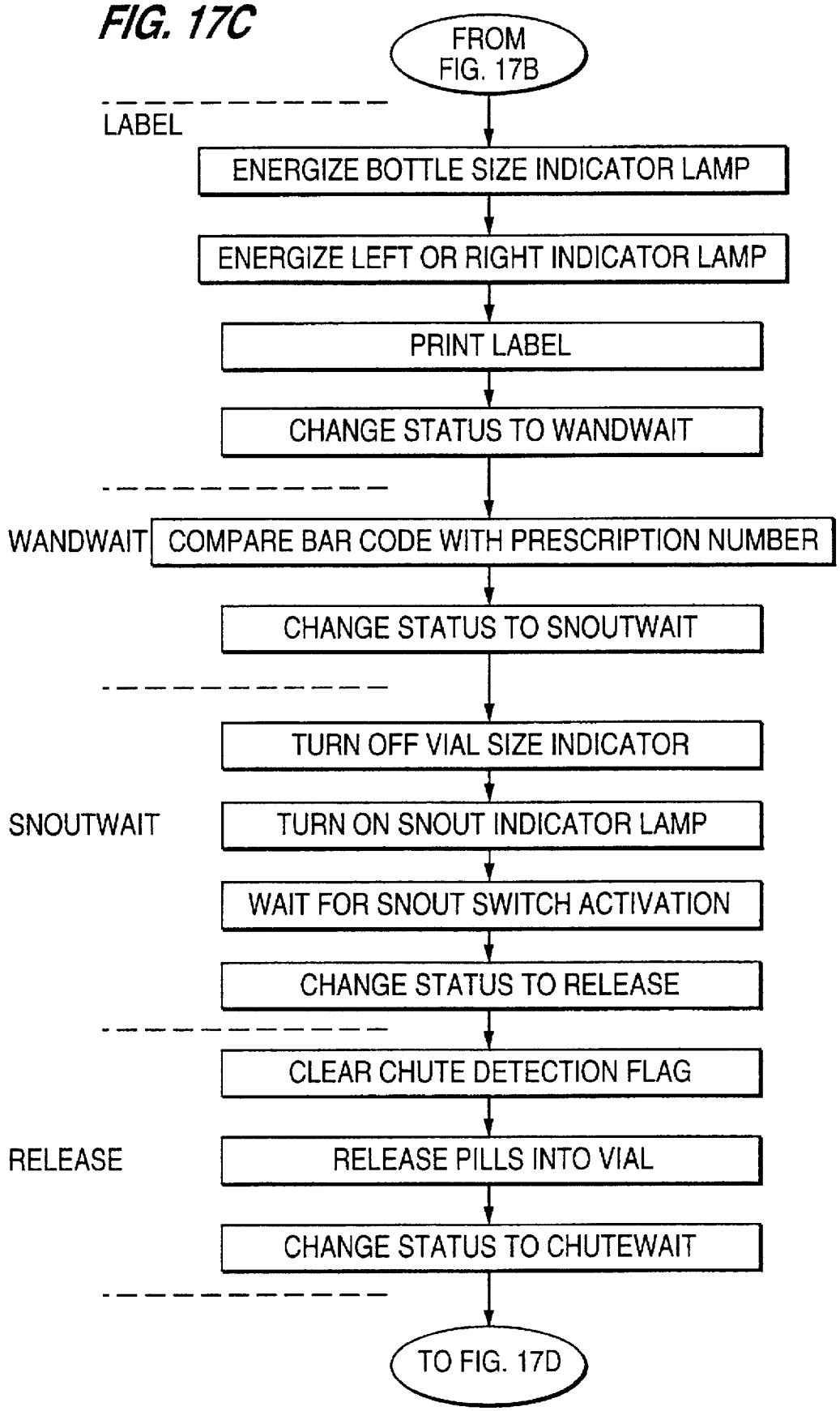

FIGS. 17a through 17d show a flowchart which represents the sequence of operations performed by the computer in the operator station routine 321 for a given script in the script buffer during successive iterations through the operator station routine. In the flowchart, the status words are shown in the left-hand column opposite the flowchart illustrative of the functions performed by the routine 321 in response to the indicated status word. The status word in each script buffer register will initially be set to READY. As shown in FIG. 17a, when the status word is READY, the computer sends a READY message to the host in the host interface routine 338. The host computer in response to receiving a READY message in the host interface routine 338 will send a script to the computer 150 to be placed in the script buffer register and, when this script has been stored in the script buffer register, the status word stored in this buffer register will be changed to PRESTART. When the status word is PRESTART, the program in a following iteration through the routine 321 checks the status of the upper hopper use flag. This flag shows whether the upper hopper is in use meaning that it contains pills. If the upper hopper use flag show the upper hopper contains pills, the program branches to cancel the prescription process by setting the status word to CANCEL. When the upper hopper use flag shows that the upper hopper is not in use, then the program in the prestart routine sets the upper hopper use flag to show that the upper hopper is now in use and changes the status word to START. After the status word has been changed to START, in the next iteration through the routine 321, the program determines the vial size to be used for the prescription from the number of pills in the prescription. The program then checks the status of the upper hopper trap door switch 85 to determine whether the upper hopper trap door is opened or closed. If the upper hopper trap door switch shows that the upper hopper door is open, the program starts a half second timer to determine whether a half second time interval has elapsed. This time interval will elapse after 10 iterations through the operator station routine with the status word remaining START. If the half second timer times out, the program will branch to change the status word to CANCEL to cancel the prescription because the upper hopper door remained open. After the computer determines that the upper hopper trap door is closed, then in the next iteration through routine 321, the program starts the dispensing cell to begin dispensing pills into the upper hopper by sending the cell number and the pill quantity in a script packet to the FIFO register 218. As described above, when the script packet is received in the FIFO register 218, the microcontroller 242 will place the character F in a corresponding status packet in the input FIFO 240 to indicate that the prescription has been accepted and that the dispensing has begun. The microcontroller 242 will then energize the selected motor and begin counting out the pills. Following the starting of the dispensing cell, the routine 321 changes the status word to STARTED. In the next iteration through cell controller interface routine 340 following the character F being stored in the status packet in the input FIFO 240, the computer will read the character F from the input FIFO indicating that the dispensing cell has been started and has begun counting out the prescription. In response to receiving the character F, the cell interface routine 340 will change the status word in the script buffer register to FILLING.

In the routine 321, when the status word is STARTED, the program determines in successive iterations through the routine whether the status word changes to FILLING within two seconds. If the status word does not change from STARTED to FILLING within two seconds, the program branches to change the status word to CANCELED to cancel the prescription. When the status word has been changed to FILLING, then the program iterates through the routine 321 successively until the status word changes to FULL. As indicated above, the microcontroller 242 will change the status character in the status packet in the input FIFO 240 to G indicating that the prescription filling has been completed when the prescription count reaches the count provided in the script packet received in the FIFO 218. When this happens, the microcontroller 242 stops the cell from counting without any further instruction from the computer 150. The computer in the cell interface routine 340 in response to receiving the status character G from the microprocessor 240 will change the status word in the script buffer register to FULL. When the status word has been changed to FULL, then in the routine 321, the program updates the dispensing cell hopper quantity by subtracting the number of pills called for to be dispensed by the prescription from the hopper quantity. As pointed out above, the hopper quantity is a value maintained by the computer for each dispensing cell representing the number of pills remaining in the input hopper of a dispensing cell. After updating the hopper quantity, the computer program determines whether the hopper quantity is low by comparing the hopper quantity with a minimum value. If the hopper quantity is low, the program branches to send a refill message by synthesized voice to the refill operator on the back side of the dispensing array. The synthesized voice indicating a low quantity of pills is also generated in response to the low level indicator in such supply hopper of the dispensing system.

In the next iteration through the operator station routine 321 while the status word is FULL, the program checks the lower hopper use flag. If the lower hopper use flag shows that the lower hopper is in use, meaning that there are pills in the lower hopper, as may be the case from an earlier prescription, the program status word will remain FULL. Accordingly, the status of this lower hopper use flag will be repeatedly checked during each successive iteration through the operator station routine. When the lower hopper use flag is cleared showing that the lower hopper is not in use and meaning that there are no pills in the lower hopper, the routine then sets the lower hopper use flag and changes the status word to DUMPING. Then in a subsequent iteration through the routine 321, when the status word is DUMPING, the program will dump the pills from the upper hopper to the lower hopper by energizing the solenoid 97. When the dumping has been completed, the routine 321 changes the status word to LABELWAIT. Then, in successive iterations, after the status word has been changed to LABELWAIT, the routine 321 clears the upper hopper use flag and then waits for that script buffer register's to turn to print a prescription label. The computer can only print one label at a time and, accordingly each script in the script buffer must wait for its turn to print the label. When the turn comes for a particular script buffer register, then a pointer will point to that script buffer register. When this happens, the program in the following iteration through routine 321 will change the status word to LABEL. Then, in a following iteration through the routine 321, after the status word has been changed to LABEL, the program will energize the bottle size indicator lamp which indicates the size of the bottle to be used by the operator. The bottle size will have been previously determined from the pill quantity as described above. Following the energization of the bottle size lamp, the program will energize the right or left indicator lamp to indicate whether the prescription will be filled from a snout on the right or left side of the operator station. Following the energization of the right or left indicator lamp, the program proceeds to the print label subroutine wherein the label is printed from the script data in the script buffer register. The printed label in addition to having the usual prescription information will also include a bar code which identifies the prescription number. Following of the printing of the label, the program changes the status word to WAND-WAIT. Then after the status word has been changed to WANDWAIT, in a following iteration through the routine 321, the program compares the prescription number indicated by the bar code read from the prescription label in routine 330 with the prescription number in the script buffer. If the bar code does not correspond to the prescription number, then program causes an error message to be displayed on the front console display screen 54. If an error message is displayed, the operator can rescan the bar code to recheck the bar code prescription number against the prescription number in the script buffer. If a match cannot be obtained, the system has malfunctioned and the program cannot proceed. Accordingly, the technician must be called to correct the malfunction. If the prescription numbers represented by the bar code is the same as the prescription number in the prescription buffer, the program changes the status word to SNOUTWAIT. After the status word has been changed to SNOUTWAIT, in a following iteration through the routine 321, the program turns off the vial size indicator and turns on the snout indicator lamp which indicates the snout from which the prescription is to be dispensed. The snout indicator lamp is selected by the cell number and slice number in the script in the prescription buffer register. The program then waits for the snout switch 108 to be activated by a vial being positioned at the snout to receive the pills released from the lower buffer. When the snout switch has been activated, the program in the routine 321 changes the status word to RELEASE. Then in a successive iteration through the routine 321, after the status word has been changed to RELEASE, the program clears a chute detection flag which is set in response to a vial containing pills being placed in the chute 32 at the operator station. Then, with the status word RELEASE, the program releases the pills into the vial by energizing the solenoid 104 to open the lower hopper trap door and then changes the status to CHUTEWAIT. After the status word has been changed to CHUTEWAIT in a later iteration through the routine 321, the program turns off the snout indicator lamp, then clears the lower hopper use flag and then waits in successive iterations through the routine 321 for the chute detection flag to be set. When the chute detection flag has been set, the program enables the next script in the script buffer to be printed by incrementing the pointer to point to the next script buffer register containing a script to be printed. The program then turns off the left and right side indicator lamps and changes the status to READY so that the control computer 150 will send a READY message to the host computer 152 to indicate that the corresponding script buffer register is ready to receive another script to be processed.

As described above, the status word gets changed to FILLING and FULL in the cell interface routine 340 in response to receiving the characters F and G from the input FIFO. If the character received in the cell interface routine is A, X, or H, the cell interface routine changes the status word to CANCELED. If the characters received in the cell interface routine is W, meaning that the pill count is slow, the cell interface routine calls on the vibration, which causes a bit to be set in the appropriate bit location of the appropriate output register 211–216 to vibrate the slow counting cell.

After a status word has been changed to CANCELED, the control computer 150 causes a message to be sent to the host computer that the prescription has been canceled, and then sets the status word in the corresponding script buffer register to READY so that the host computer can send another script to be stored in the script buffer register.

As indicated above, a step of the above described process illustrated in FIGS. 17a through 17d is performed for each of the five scripts in the script buffer registers each time the program iterates through the operator station routine 321. Each script buffer register may have a different status word and, accordingly, the program will perform different steps of the dispensing process for each script in the script buffer register. Thus, while the label for one script is being printed, the pills for other scripts may be in the process of being counted, being dumped from the upper hopper to the lower hopper, or be waiting in the lower hopper for their scripts turn to have a label printed. In this manner, the dispensing operation for up to five prescriptions can be processed simultaneously. However, only one printer is provided so each script must wait its turn for printing a label. To reduce the chances of error, a new label will not be printed until the filled prescription of the previous label has been deposited in the chute. Accordingly, the last part of the dispensing process from printing the label to detecting the filled prescription vial in the chute is performed for only one script at a time.

It will be apparent to those skilled in the art and it is contemplated that variations and/or changes in the embodiments illustrated and described herein maybe made without departure from the present invention. Accordingly, it is intended that the foregoing description is illustrative only, not limiting, and that the true spirit and scope of the present invention will be determined by the appended claims.

We claim:

1. An automated prescription dispensing system comprising a plurality of adjacently arranged pill dispensers, each operable to count out and dispense pills of a different pharmaceutical, computer control means to store a plurality of prescriptions each specifying a different pharmaceutical in pill form and a number of pills, said computer control means selecting the pill dispensers dispensing the pharmaceuticals specified in said stored prescriptions and controlling the selected pill dispensers to simultaneously count out and dispense pills, said computer control means stopping each pill dispenser from counting out and dispensing pills when the number of pills specified in the corresponding prescription have been counted out and dispensed, a plurality of upper hoppers, one for each of said pill dispensers, positioned to receive pills counted out and dispensed by said pill dispensers, a plurality of lower hoppers one for each of said upper hoppers, said computer control means releasing pills from an upper hopper into the corresponding lower hoppers after the pills of a prescription have been dispensed into such upper hopper, said computer means selectively permitting the release of pills from said lower hoppers into prescription containers.

2. An article dispensing system comprising:
a supply hopper for a plurality of articles to be dispensed;
a first buffer chamber having an outlet and an outlet door;
means for counting and advancing articles from the supply hopper to said first buffer chamber;
first means for moving said outlet door to release the articles from said first buffer chamber in response to a first predetermined condition;
a second buffer chamber for receiving articles from said first buffer chamber, said second buffer chamber having an outlet and an outlet door; and
second means for moving said door of said second buffer chamber to release the articles from said second buffer chamber in response to a second predetermined condition.

3. The article dispensing system of claim 2, wherein said second means will not move the outlet door of said second buffer chamber to release the articles from said second buffer chamber until after verification by machine reading of a bar-coded prescription on a receptacle for receiving the articles.

4. The article dispensing system of claim 2, wherein said second means comprises means for moving said outlet door of said second buffer chamber to release the articles from said second buffer chamber in response to the presence of a receptacle at an outlet snout.

5. The article dispensing system of claim 2, further comprising a cabinet having a rear wall, wherein said supply hopper is positioned inside said cabinet, said rear wall has an opening for providing access to said supply hopper, the article dispensing system further comprising a security door movably mounted on said rear wall, said security door being movable between a first position, in which said security door covers said opening, and a second position, in which said security door uncovers said opening, and locking means for preventing movement of said door from its first position.

6. The article dispensing system of claim 5, further comprising means for disabling said locking means, so that said security door can be moved out of said first position.

7. The article dispensing system of claim 6, wherein said actuating disabling means comprises a bar code reader.

8. An article dispensing system comprising:
a plurality of article dispensing subsystems each including a supply hopper for a plurality of articles to be dispensed;
a first buffer chamber having an outlet and an outlet door;
means for counting and advancing articles from the supply hopper to said first buffer chamber;
first means for moving said outlet door to release the articles from said first buffer chamber in response to a first predetermined condition;
a second buffer chamber for receiving articles from said first buffer chamber, said second buffer chamber having an outlet and an outlet door; and
second means for moving said door of said second buffer chamber to release the articles from said second buffer chamber in response to a second predetermined condition.

9. The article dispensing system of claim 8, wherein each of a plurality of the article dispensing subsystems contains pills different from pills contained by other article dispensing subsystems, and the article dispensing system further comprises means for actuating the article counting and advancing means of one of the subsystems in response to a prescription, means for printing a corresponding bar-coded prescription label, and means for indicating the location of a container suitable to hold the prescription.

10. The article dispensing system of claim 9, further comprising machine means for reading the bar-coded label and wherein said second means will not move the door of said second buffer chamber to release the pills until after verification by reading of the bar-coded label by the reading means.

11. The article dispensing system of claim 10, wherein each of the article dispensing systems includes an outlet snout through which the pills are dispensed to a receptacle, and an indicator associated with each snout, the article dispensing system further comprising means for actuating the indicator of the snout through which the pills are to be dispensed.

12. The article dispensing system of claim 9, wherein said means for printing a bar-coded label comprises means for printing a series of bar-coded labels, each label being associated with a prescription to be filled, the article dispensing system further comprising means responsive to the presence of a receptacle at the outlet snout through which a current prescription is being filled.

13. The article dispensing system of claim 8, further comprising a cabinet having a rear wall, wherein each of said supply hoppers is positioned inside said cabinet, said rear wall has a plurality of openings, each said opening provides access to a respective one of said supply hoppers, said rear wall also has a plurality of security doors, each said security door is associated with a respective one of said openings and is movable between a first position, in which said security door covers said opening, and a second position, in which said security door uncovers said opening, and the article dispensing system further comprises locking means for preventing movement of said security doors from their first positions, and means for disabling said locking means of one of said security doors in response to the machine reading of a bar-coded label on a supply container of pills.

14. The article dispensing system of claim 13, further comprising an indicator associated with each of said security doors, and means for actuating one of said indicators in response to the machine reading of a bar-coded label on a supply container of pills.

15. The article dispensing system of claim 10, further comprising a first bank of outlet snouts, each associated with one of said article dispensing subsystems, positioned on one side of said machine means for reading the bar-coded label, a second bank of outlet snouts, each associated with one of said article dispensing subsystems, positioned on an opposite side of said machine means for reading the label, an indicator associated with each bank of outlet snouts, and means for actuating the indicator of the bank at which the pills required by the bar-coded label are to be dispensed.

16. An automated prescription dispensing system comprising a plurality of adjacently arranged pill dispensers, each operable to count out and dispense pills of a different pharmaceutical, computer control means to store a plurality of prescriptions each specifying a different pharmaceutical in pill form and a number of pills, said computer control means selecting the pill dispensers dispensing the pharmaceuticals specified in said stored prescriptions and controlling the selected pill dispensers to simultaneously count out and dispense pills, said computer control means stopping each pill dispenser from counting out and dispensing pills when the number of pills specified in the corresponding prescription have been counted out and dispensed, and label means to produce prescription container labels, said computer control means causing said label means to produce prescription labels containing information corresponding to said stored prescriptions, wherein said label means produces said prescription labels one at a time and will not produce a prescription label for the next prescription until after pills specified in a preceding prescription have been received from a pill dispenser into a prescription container.

17. An automated dispensing system as recited in claim 16, wherein a plurality of output hoppers are provided, one for each of said pill dispensers to receive the pills counted out and dispensed by said pill dispensers, said computer control means including means to selectively permit the release of the pills from said output hoppers into prescription pill containers.

18. An automated prescription dispensing system as recited in claim 16, wherein signalling means are provided for each of said pill dispensers to call an operator's attention to such pill dispenser when such indicating means is activated, said computer control means being responsive to said stored prescriptions to select and activate one of said indicating means.

19. An automated prescription dispensing system comprising a plurality of adjacently arranged pill dispensers, each operable to count out and dispense pills of a different pharmaceutical, computer control means to store a plurality of prescriptions each specifying a different pharmaceutical in pill form and a number of pills, each computer control means selecting the pill dispensers dispensing the pharmaceuticals specified in said stored prescriptions and controlling the selected pill dispensers to simultaneously count out and dispense pills, said computer control means stopping each pill dispenser from counting out and dispensing pills when the number of pills specified in the corresponding prescription have been counted out and dispensed, a plurality of output hoppers one for each of said pill dispensers to receive the pills counted out and dispensed by said pill dispensers, output snouts, one connected to each of said output hoppers, said computer control means including means to selectively permit the release of the pills from said output hoppers through the corresponding output snouts, said output snouts being arranged in at least one row and defining an aisle extending adjacent to and parallel to said row to permit an operator to have ease of access to pills dispensed through said snouts.

20. An article dispensing system comprising a plurality of adjacently arranged article dispensing subsystems each including a supply hopper for a plurality of articles to be dispensed, means for counting out and dispensing articles from a selected supply hopper, said system including a cabinet having a rear wall and a front side wall wherein the supply hoppers are positioned inside said cabinet, said dispensing subsystems dispensing said articles from said front side, said rear wall having a plurality of openings, each of said openings providing access to a respective one of said supply hoppers, said rear wall also having a plurality of security doors, each of said security doors being associated with a respective one of said openings and being movable between a first position in which said security door covers said opening and a second position in which said security door uncovers said opening, the article dispensing system further comprising locking means for preventing movement of said security doors from their first positions, and means for disabling said locking means of one of said security doors in response to the machine reading of a bar coded label on the supply container of articles to be dispensed by the article dispensing system.

21. A pharmaceutical pill dispensing system comprising a plurality of pill dispensers each operable to store a plurality of pills to be dispensed in a supply hopper and to count and dispense pills from the corresponding supply hopper, computer control means to select one of said dispensers and to operate the selected dispensers to count out and dispense a preselected number of pills, each computer control means maintaining a hopper quantity for each of said dispensers representing the number of pills in the hopper of such dispenser and reducing the hopper quantity of each dispenser by the preselected number counted out by such dispenser when the selected dispenser is caused to count out the preselected number of pills, said computer control means including means to provide an indication to an operator when the hopper quantity of one of said dispensers falls below a predetermined minimum, and means to increase the hopper quantity for each dispenser when pills are added to the supply hopper of such dispenser by the number of pills added to the supply hopper of a corresponding pill dispenser.

22. An automated pill dispensing system as recited in claim 21, wherein said means to increase said hopper quantity includes a bar code reader to read a bar code on a bulk supply container of pills to be added to the supply hopper of a given pill dispenser.

23. A method of dispensing prescriptions employing a plurality of adjacently arranged pill dispensers operable to count out and dispense pills and employing a computer to control the operation of said dispensers comprising the steps of storing a supply of pills of a different pharmaceutical in each said pill dispensers, storing a plurality of prescriptions to be filled in a memory of said computer, said prescriptions each containing the identification of a pharmaceutical pill to be dispensed and a prescribed number of pills, programming said computer to select the pill dispensers storing the pills identified by prescriptions stored in said computer memory, and operating the selected dispensers to simultaneously count out and dispense the prescribed number of pills in response to the prescriptions stored in said memory, receiving the pills counted out by each dispenser into a corresponding upper hopper, releasing the pills from said upper hopper into a corresponding lower hopper when the counting and dispensing by the corresponding dispenser has been completed, positioning vials to receive pills from the lower hoppers which have received pills, and releasing pills from the lower output hoppers into said vials.

24. A method of dispensing prescriptions s recited in claim 23 further comprising printing a label for each of the prescriptions stored in said memory of said computer, said label containing the prescription information of the prescriptions stored in the memory of said computer, applying the printed labels to prescription vials and filling the labeled prescription vials with the pills counted out and dispensed by said selected dispensers.

25. A method of dispensing prescriptions as recited in claim 24 wherein the sequence of printing a label, applying the label to a vial and receiving pills into a labeled vial are carried out for one prescription at a time.

26. A method of dispensing prescriptions as recited in claim 23 wherein the pills are released from the lower hoppers into prescription vials one vial at a time.

27. A method of dispensing prescriptions as recited in claim 24 further comprising printing a bar code on each prescription label representing a prescription number identifying the corresponding prescription and verifying the prescription number with a bar code reader before filling the labeled vial with pills.

* * * * *